(12) United States Patent
Malinouskas et al.

(10) Patent No.: US 10,105,140 B2
(45) Date of Patent: Oct. 23, 2018

(54) SURGICAL CONSOLE AND HAND-HELD SURGICAL DEVICE

(75) Inventors: Donald Malinouskas, Monroe, CT (US); David A. Zeichner, Oxford, CT (US); Michael P. Whitman, New Hope, PA (US); David A. Nicholas, Trumbull, CT (US); Xingrui Chen, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/758,900

(22) Filed: Apr. 13, 2010

(65) Prior Publication Data

US 2011/0125138 A1 May 26, 2011

Related U.S. Application Data

(63) Continuation-in-part of application No. 12/622,827, filed on Nov. 20, 2009.

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 90/90* (2016.02); *A61B 90/92* (2016.02); *A61B 90/98* (2016.02); *A61B 34/10* (2016.02); *A61B 2017/00115* (2013.01); *A61B 2017/00119* (2013.01);
(Continued)

(58) Field of Classification Search
CPC ..... A61B 17/00–17/7225; A61B 19/00–19/56; A61B 2019/0201–2019/568; A61B 34/00; A61B 17/0004–17/505
See application file for complete search history.

(56) References Cited

U.S. PATENT DOCUMENTS

| 4,722,685 A | 2/1988 | de Estrada et al. |
| 4,823,807 A | 4/1989 | Russell et al. |

(Continued)

FOREIGN PATENT DOCUMENTS

| AU | 2008229795 A1 | 4/2009 |
| CA | 2451558 | 1/2003 |

(Continued)

OTHER PUBLICATIONS

European Search Report for EP 11 25 0462 application, date of completion, Jul. 20, 2011.

(Continued)

*Primary Examiner* — Lynsey Eiseman

(57) ABSTRACT

A surgical system and method includes a surgical instrument configured to wirelessly transmit identifying data specific to the surgical instrument and a console configured to receive the identifying data. The console is configured to register the surgical instrument based on the identifying data, establish a wireless two-way communication link between the surgical instrument and the console, receive at least one of operational data and commands from the surgical instrument, and provide operational feedback data to a user of the surgical instrument during an operation of the surgical instrument based on the at least one of operational data and commands.

13 Claims, 16 Drawing Sheets

(51) Int. Cl.
*A61B 90/90* (2016.01)
*A61B 90/92* (2016.01)
*A61B 90/98* (2016.01)
*A61B 17/00* (2006.01)
*A61B 90/00* (2016.01)
*A61B 34/10* (2016.01)

(52) U.S. Cl.
CPC ........... *A61B 2017/00199* (2013.01); *A61B 2017/00203* (2013.01); *A61B 2017/00212* (2013.01); *A61B 2017/00221* (2013.01); *A61B 2017/00225* (2013.01); *A61B 2017/00398* (2013.01); *A61B 2017/00464* (2013.01); *A61B 2017/00482* (2013.01); *A61B 2017/00734* (2013.01); *A61B 2017/07214* (2013.01); *A61B 2090/0803* (2016.02); *A61B 2090/0807* (2016.02); *A61B 2090/372* (2016.02)

(56) References Cited

U.S. PATENT DOCUMENTS

| | | | |
|---|---|---|---|
| 5,169,225 A | 12/1992 | Palm | |
| 5,213,913 A * | 5/1993 | Anthony, III | B25F 5/02 292/244 |
| 5,230,261 A * | 7/1993 | Akazawa | B25B 21/00 81/177.4 |
| 5,269,733 A * | 12/1993 | Anthony, III | B25B 21/026 173/171 |
| 5,301,061 A | 4/1994 | Nakada et al. | |
| 5,411,508 A | 5/1995 | Bessler et al. | |
| 5,427,087 A | 6/1995 | Ito et al. | |
| 5,540,375 A | 7/1996 | Bolanos et al. | |
| 5,540,706 A | 7/1996 | Aust et al. | |
| 5,549,637 A | 8/1996 | Crainich | |
| 5,553,675 A | 9/1996 | Pitzen et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,658,300 A | 8/1997 | Bito et al. | |
| 5,693,042 A | 12/1997 | Boiarski et al. | |
| 5,762,603 A | 6/1998 | Thompson | |
| 5,782,396 A | 7/1998 | Mastri et al. | |
| 5,792,573 A | 8/1998 | Pitzen et al. | |
| 5,797,670 A * | 8/1998 | Snoke | B25B 23/18 24/16 PB |
| 5,865,361 A | 2/1999 | Milliman et al. | |
| 5,881,418 A * | 3/1999 | Enoch | 15/101 |
| 6,010,054 A | 1/2000 | Johnson et al. | |
| 6,032,849 A | 3/2000 | Mastri et al. | |
| 6,126,651 A | 10/2000 | Mayer | |
| 6,165,169 A | 12/2000 | Panescu et al. | |
| 6,237,604 B1 | 5/2001 | Burnside et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,302,692 B1 * | 10/2001 | Pond | A61C 1/0076 433/100 |
| 6,371,909 B1 | 4/2002 | Hoeg et al. | |
| 6,434,507 B1 | 8/2002 | Clayton | |
| 6,436,107 B1 * | 8/2002 | Wang | A61B 34/77 318/568.11 |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,716,233 B1 | 4/2004 | Whitman | |
| 6,743,240 B2 | 6/2004 | Smith et al. | |
| 6,783,533 B2 | 8/2004 | Green et al. | |
| 6,793,652 B1 | 9/2004 | Whitman et al. | |
| 6,830,174 B2 | 12/2004 | Hillstead et al. | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,851,487 B1 * | 2/2005 | Shotey | B25F 5/00 173/1 |
| 6,905,057 B2 | 6/2005 | Swayze et al. | |
| 6,961,974 B1 * | 11/2005 | Goolsby, Jr. | B08B 1/04 15/104.04 |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| RE39,152 E | 6/2006 | Aust et al. | |
| 7,059,508 B2 | 6/2006 | Shelton, IV et al. | |
| 7,077,856 B2 | 7/2006 | Whitman | |
| 7,122,029 B2 | 10/2006 | Koop et al. | |
| 7,140,528 B2 | 11/2006 | Shelton, IV | |
| 7,147,138 B2 | 12/2006 | Shelton | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,407,078 B2 | 8/2008 | Shelton, IV et al. | |
| 7,481,824 B2 | 1/2009 | Boudreaux et al. | |
| 7,565,993 B2 | 7/2009 | Milliman et al. | |
| 7,575,144 B2 | 8/2009 | Ortiz et al. | |
| 7,588,175 B2 | 9/2009 | Timm et al. | |
| 7,699,835 B2 | 4/2010 | Lee et al. | |
| 7,738,971 B2 | 6/2010 | Swayze et al. | |
| 7,793,812 B2 | 9/2010 | Moore et al. | |
| 7,803,151 B2 | 9/2010 | Whitman | |
| 7,822,458 B2 | 10/2010 | Webster, III et al. | |
| 7,845,534 B2 | 12/2010 | Viola et al. | |
| 7,857,185 B2 | 12/2010 | Swayze et al. | |
| 7,870,989 B2 | 1/2011 | Viola et al. | |
| 7,922,061 B2 | 4/2011 | Shelton, IV et al. | |
| 7,922,719 B2 | 4/2011 | Ralph et al. | |
| 7,947,034 B2 | 5/2011 | Whitman | |
| 7,954,682 B2 | 6/2011 | Giordano et al. | |
| 7,959,051 B2 | 6/2011 | Smith et al. | |
| 7,967,179 B2 | 6/2011 | Olson et al. | |
| 8,016,178 B2 | 9/2011 | Olson et al. | |
| 8,025,199 B2 | 9/2011 | Whitman et al. | |
| 8,035,487 B2 | 10/2011 | Malackowski | |
| 8,052,024 B2 | 11/2011 | Viola et al. | |
| 8,056,787 B2 | 11/2011 | Boudreaux et al. | |
| 8,114,118 B2 | 2/2012 | Knodel et al. | |
| 8,132,705 B2 | 3/2012 | Viola et al. | |
| 8,152,516 B2 | 4/2012 | Harvey et al. | |
| 8,157,150 B2 | 4/2012 | Viola et al. | |
| 8,182,494 B1 | 5/2012 | Yencho et al. | |
| 8,186,587 B2 | 5/2012 | Zmood et al. | |
| 8,235,273 B2 | 8/2012 | Olson et al. | |
| 8,272,554 B2 | 9/2012 | Whitman et al. | |
| 8,292,150 B2 | 10/2012 | Bryant | |
| 8,303,581 B2 | 11/2012 | Arts et al. | |
| 8,342,379 B2 | 1/2013 | Whitman et al. | |
| 8,348,855 B2 | 1/2013 | Hillely et al. | |
| 8,353,440 B2 | 1/2013 | Whitman et al. | |
| 8,365,633 B2 | 2/2013 | Simaan et al. | |
| 8,371,492 B2 | 2/2013 | Aranyi et al. | |
| 8,424,739 B2 | 4/2013 | Racenet et al. | |
| 8,454,585 B2 | 6/2013 | Whitman | |
| 8,505,802 B2 | 8/2013 | Viola et al. | |
| 8,517,241 B2 | 8/2013 | Nicholas et al. | |
| 8,551,076 B2 | 10/2013 | Duval et al. | |
| 8,561,871 B2 | 10/2013 | Rajappa et al. | |
| 8,623,000 B2 | 1/2014 | Humayun et al. | |
| 8,632,463 B2 | 1/2014 | Drinan et al. | |
| 8,647,258 B2 | 2/2014 | Aranyi et al. | |
| 8,657,174 B2 | 2/2014 | Yates et al. | |
| 8,696,552 B2 | 4/2014 | Whitman | |
| 8,708,213 B2 | 4/2014 | Shelton, IV et al. | |
| 8,752,749 B2 | 6/2014 | Moore et al. | |
| 8,758,391 B2 | 6/2014 | Swayze et al. | |
| 8,806,973 B2 | 8/2014 | Ross et al. | |
| 8,851,355 B2 | 10/2014 | Aranyi et al. | |
| 8,858,571 B2 | 10/2014 | Shelton, IV et al. | |
| 8,875,972 B2 | 11/2014 | Weisenburgh, II et al. | |
| 8,893,946 B2 | 11/2014 | Boudreaux et al. | |
| 8,899,462 B2 | 12/2014 | Kostrzewski et al. | |
| 8,939,344 B2 | 1/2015 | Olson et al. | |
| 8,960,519 B2 | 2/2015 | Whitman et al. | |
| 8,961,396 B2 | 2/2015 | Azarbarzin et al. | |

(56) References Cited

U.S. PATENT DOCUMENTS

| | | | |
|---|---|---|---|
| 8,967,443 B2 | 3/2015 | McCuen | |
| 8,968,276 B2 | 3/2015 | Zemlok et al. | |
| 8,968,337 B2 | 3/2015 | Whitfield et al. | |
| 8,992,422 B2 | 3/2015 | Spivey et al. | |
| 9,064,653 B2 | 6/2015 | Prest et al. | |
| 9,113,875 B2 | 8/2015 | Viola et al. | |
| 9,216,013 B2 | 12/2015 | Scirica et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0125717 A1 | 7/2003 | Whitman | |
| 2003/0143042 A1* | 7/2003 | Doyle | B25B 23/141 408/124 |
| 2003/0165794 A1 | 9/2003 | Matoba | |
| 2004/0013486 A1* | 1/2004 | Cooper | B25F 5/006 408/241 R |
| 2004/0111081 A1 | 6/2004 | Whitman et al. | |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0230223 A1* | 11/2004 | Bonutti et al. | 606/232 |
| 2005/0096684 A1 | 5/2005 | Farrow et al. | |
| 2005/0101963 A1* | 5/2005 | Merboth et al. | 606/92 |
| 2005/0131442 A1 | 6/2005 | Yachia et al. | |
| 2005/0135084 A1* | 6/2005 | Chen | B25B 21/00 362/109 |
| 2005/0192609 A1 | 9/2005 | Whitman et al. | |
| 2006/0142740 A1 | 6/2006 | Sherman et al. | |
| 2006/0267548 A1* | 11/2006 | Uehlein-Proctor et al. | 320/107 |
| 2006/0278680 A1 | 12/2006 | Viola et al. | |
| 2007/0023476 A1 | 2/2007 | Whitman et al. | |
| 2007/0055219 A1 | 3/2007 | Whitman et al. | |
| 2007/0055304 A1 | 3/2007 | Whitman | |
| 2007/0152014 A1 | 7/2007 | Gillum et al. | |
| 2007/0175961 A1 | 8/2007 | Shelton et al. | |
| 2007/0201748 A1* | 8/2007 | Bixler | B25F 5/001 382/225 |
| 2007/0255296 A1* | 11/2007 | Sauer | 606/144 |
| 2008/0109012 A1 | 5/2008 | Falco et al. | |
| 2008/0110958 A1 | 5/2008 | McKenna et al. | |
| 2008/0167736 A1 | 7/2008 | Swayze et al. | |
| 2008/0188841 A1 | 8/2008 | Tomasello et al. | |
| 2008/0197167 A1 | 8/2008 | Viola et al. | |
| 2008/0212026 A1* | 9/2008 | Molnar | A61B 3/14 351/206 |
| 2008/0237296 A1 | 10/2008 | Boudreaux et al. | |
| 2008/0255413 A1 | 10/2008 | Zemlok et al. | |
| 2008/0255505 A1* | 10/2008 | Carlson et al. | 604/95.04 |
| 2008/0262654 A1 | 10/2008 | Omori et al. | |
| 2008/0296373 A1 | 12/2008 | Zmood et al. | |
| 2008/0308603 A1 | 12/2008 | Shelton et al. | |
| 2009/0090763 A1 | 4/2009 | Zemlok et al. | |
| 2009/0099876 A1 | 4/2009 | Whitman | |
| 2009/0101692 A1 | 4/2009 | Whitman et al. | |
| 2009/0171147 A1 | 7/2009 | Lee et al. | |
| 2009/0209957 A1 | 8/2009 | Schmaltz et al. | |
| 2009/0254094 A1 | 10/2009 | Knapp et al. | |
| 2009/0299141 A1* | 12/2009 | Downey | A61B 17/2909 600/118 |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 | 7/2011 | Ross et al. | |
| 2011/0204119 A1 | 8/2011 | McCuen | |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0181035 A1 | 7/2013 | Milliman | |
| 2013/0184704 A1 | 7/2013 | Beardsley et al. | |
| 2013/0214025 A1 | 8/2013 | Bryant | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2014/0110455 A1 | 4/2014 | Ingmanson et al. | |
| 2014/0207125 A1 | 7/2014 | Applegate et al. | |
| 2014/0207182 A1 | 7/2014 | Zergiebel et al. | |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | |
|---|---|---|
| CN | 101035482 A | 9/2007 |
| CN | 101094617 A | 12/2007 |
| CN | 101283924 A | 10/2008 |
| CN | 101856251 A | 10/2010 |
| CN | 102 247 182 | 11/2011 |
| DE | 20220934 U1 | 7/2004 |
| DE | 102008053842 A1 | 5/2010 |

(56) References Cited

FOREIGN PATENT DOCUMENTS

| | | | |
|---|---|---|---|
| EP | 0648476 A1 | 4/1995 |
| EP | 0686374 A2 | 12/1995 |
| EP | 0705571 A1 | 4/1996 |
| EP | 1676540 A1 | 7/2006 |
| EP | 1690502 A1 | 8/2006 |
| EP | 1723913 A1 | 11/2006 |
| EP | 1736112 | 12/2006 |
| EP | 1759652 A2 | 3/2007 |
| EP | 1772105 A1 | 4/2007 |
| EP | 1813199 | 8/2007 |
| EP | 1813211 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943976 A2 | 7/2008 |
| EP | 1952769 A2 | 8/2008 |
| EP | 2 005 898 | 12/2008 |
| EP | 2027819 A1 | 2/2009 |
| EP | 2044890 A1 | 4/2009 |
| EP | 2090247 A1 | 8/2009 |
| EP | 2100561 A2 | 9/2009 |
| EP | 2100562 A2 | 9/2009 |
| EP | 2164290 A1 | 3/2010 |
| EP | 2165664 A2 | 3/2010 |
| EP | 2236098 | 10/2010 |
| EP | 2245994 A1 | 11/2010 |
| EP | 2263568 | 12/2010 |
| EP | 2272443 A1 | 1/2011 |
| EP | 2316345 A1 | 5/2011 |
| EP | 2324776 A2 | 5/2011 |
| EP | 2329773 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 | 5/2013 |
| EP | 2606834 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 3018959 U | 12/1995 |
| JP | 08-038488 | 2/1996 |
| JP | 2001244972 A | 9/2001 |
| JP | 2005-125075 A | 5/2005 |
| JP | 2008246188 A | 10/2008 |
| KR | 20120022521 A | 3/2012 |
| WO | 94/14129 A1 | 6/1994 |
| WO | 99/15086 A1 | 4/1999 |
| WO | WO2000/72760 A1 | 12/2000 |
| WO | WO 2003/000138 | 1/2003 |
| WO | 2003/030743 A2 | 4/2003 |
| WO | 0347450 A2 | 6/2003 |
| WO | 2003065916 A1 | 8/2003 |
| WO | 2003090630 A2 | 11/2003 |
| WO | WO2004/107989 | 12/2004 |
| WO | WO2006/042210 A2 | 4/2006 |
| WO | 2007016290 A2 | 2/2007 |
| WO | 2007026354 A1 | 3/2007 |
| WO | WO2007/026354 | 3/2007 |
| WO | 2007137304 A2 | 11/2007 |
| WO | WO2008/131362 | 10/2008 |
| WO | WO2008/133956 | 11/2008 |
| WO | 2009039506 A1 | 3/2009 |
| WO | 2009/132359 A2 | 10/2009 |
| WO | WO2009/132359 A2 | 10/2009 |
| WO | 2009/143092 A1 | 11/2009 |
| WO | 2009149234 A1 | 12/2009 |
| WO | WO 2011/108840 | 9/2011 |
| WO | 2012040984 A1 | 4/2012 |

OTHER PUBLICATIONS

European Search Report for EP 10 25 1968 application, date of completion, Jul. 4, 2011.
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to EP No. 11 17 8021.9, dated Jun. 4, 2013; (3pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
Chinese Office Action Application No. 201110097438.2 dated Dec. 17, 2014 and translation.
European Search Report, Application No. 15 15 1076 dated Apr. 22, 2015.
Australian Examiner's Report issued in Application No. AU 2010241367 dated Aug. 20, 2015.
European Office Action dated Jul. 12, 2016 in corresponding European Patent Application No. 15151076.5, 5 pages.
Canadian Office Action dated Nov. 2, 2016 in corresponding Canadian Patent Application No. 2734160, 3 pages.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.

(56) References Cited

OTHER PUBLICATIONS

International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Japanese Office Action, with English language translation, issued in Japanese Appl. No. JP 2011-084092 dated Jan. 12, 2016 (5 pages).
European Search Report dated Jun. 15, 2016 in corresponding European Patent Application No. EP 16 15 0144, 6 pages.
European Office Action dated Apr. 6, 2017 in corresponding European Patent Application No. 12197970.2, 3 pages.
Chinese Office Action dated Apr. 28, 2017 in Chinese Patent Application No. 201510994508.2 together with English translation, 18 pages.
Australian Examination Report dated Mar. 17, 2017 in corresponding Australian Patent Application No. 2016202962, 3 pages.
Canadian Office Action dated Apr. 7, 2017 in corresponding Canadian Patent Application No. 2,720,209, 3 pages.
European Office Action dated Feb. 17, 2017 in corresponding European Patent Application No. 15151076.5, 5 pages.
Australian Examination Report for application No. 2016202962 dated Jul. 3, 2017.
Chinese Office Action for application No. 2016100531828 dated Jun. 28, 2017.
Notice of Allowance dated Oct. 16, 2017 issued in corresponding Japanese Application No. 2013-112661 (JPO Communication Summary Form attached).
European Examination Report dated Sep. 1, 2017 issued in corresponding European Application No. 16150144.0.
Chinese Office Action (with English translation) dated May 9, 2018, corresponding to counterpart Chinese Application No. 2016100531828; 16 total pages.
Chinese Office Action dated Jan. 15, 2018 issued in corresponding Chinese Application No. 2015109945082.

\* cited by examiner

SURGICAL CONSOLE AND HAND-HELD SURGICAL DEVICE

CROSS-REFERENCE TO RELATED APPLICATIONS

The present application is a Continuation-in-Part Application claiming the benefit of and priority to U.S. application Ser. No. 12/622,827, filed on Nov. 20, 2009, the entire content of which is incorporated herein by reference.

FIELD OF THE INVENTION

The present invention relates generally to a surgical console and a hand-held surgical device.

BACKGROUND INFORMATION

A battery-operated, hand-held, self-contained surgical device is described, for example, in U.S. Published Patent Application No. 2009/0101692, which is expressly incorporated herein in its entirety by reference thereto, and illustrated therein with reference number 800. The device includes a circuit board to control various functions, e-g., articulation, rotation, and closing of jaws and actuation of a stapling and cutting mechanism, in response to manual inputs from a device operator, e.g., a surgeon. By not being physically connected to any external drive system, this device provides mobility during surgical procedures.

It is considered desirable to provide a two-way communication arrangement that does not reduce, or does not substantially reduce, the mobility provided by devices such as the surgical device described above. Further, it is considered desirable to register one or more surgical devices and maintain a list of registered and/or unregistered devices.

It is also considered desirable to provide a mechanism for tracking information related to, e.g., inventory, a number of uses of the device and/or attachment or device component, malfunctions, cleaning/sanitization status, and/or a number of uses between servicing. Such information may also include images acquired by an imaging device and/or a record of the device controls operated during a given procedure, e.g., a record of what inputs or controls were used by the operator, when and/or for how long they were used, and/or resulting conditions and/or parameters, such as, e.g., motor forces, component positions, and/or data obtained from sensors. Moreover, it may be desirable to provide visual and/or auditory feedback to the operator based on the received information.

Moreover, a system that prevents the use of certain devices such as, e.g., devices that have not been cleaned subsequent to a previous use, and/or unregistered devices, is considered desirable.

It is also considered desirable to provide an intelligent drive unit that provides mobility and flexibility in what types of procedures may be performed.

SUMMARY

According to an example embodiment of the present invention, a surgical system includes a surgical instrument configured to wirelessly transmit identifying data specific to the surgical instrument, and a console configured to receive the identifying data. The console is further configured to register the surgical instrument based on the identifying data, establish a wireless two-way communication link between the surgical instrument and the console, receive at least one of operational data and commands from the surgical instrument, and provide operational feedback data to a user of the surgical instrument during an operation of the surgical instrument based on the at least one of operational data and commands.

The console may have a display screen configured to visually display at least a portion of the feedback data.

The display screen may be a touch-screen display configured to receive user commands.

The console may have a speaker configured to provide at least a portion feedback data as an audio signal.

The feedback data may include at least one of an instruction and a query.

The feedback data may include an operational parameter of the surgical instrument.

The surgical device is configured to be at least partially inoperable when the surgical instrument is not registered with the console.

The surgical instrument may be a hand-held, battery-powered surgical device.

The hand-held, battery-powered surgical device may include an intelligent drive unit configured to receive different types of surgical attachments.

One of the different types of surgical attachments may be a surgical cutter/stapler.

The console may have a visual display screen configured to at least one of a) communicate the operational data and b) receive the user commands.

One or both of the surgical device and the console may be configured to operate as FCC-registered devices in one or more of the industrial, scientific, and medical (ISM) radio bands.

The console may be configured to upload operating software to the surgical instrument, the surgical instrument being configured to execute the operating software.

The surgical instrument may be configured to stream video data corresponding to a surgical procedure.

The surgical instrument and the console may be configured to operate as FCC-registered devices in one or more of the industrial, scientific, and medical (ISM) radio bands.

The industrial, scientific, and medical radio bands may include the 2.400 to 2.500 GHz ISM band.

According to an example embodiment of the present invention, a surgical device includes a hand-held, battery-powered drive unit having a housing and a mounting portion configured to accept a corresponding portion of a surgical attachment. The drive unit also includes an actuator configured to actuate at least one connection member, the connection member mating with a corresponding member of the attachment when the attachment is mounted to the mounting portion to allow the actuation of the at least one connection member to drive the attachment. The drive unit further includes a user control element configured to register a user command and a processor disposed in the housing and configured to receive a user input signal from the user control element corresponding to the user command, the processor configured to control the actuation of the connection member according to an operating program as a function of the user input signal. The drive unit also includes a transceiver configured to communicate at least one of operational data and commands to and from a remote console via a wireless two-way communication link.

The processor may be configured to control the actuation of the at least one connection member by adjusting an output voltage driving the actuator.

The drive unit may be configured to determine a serial number corresponding to the attachment.

The drive unit may be configured to determine an attachment type corresponding to the attachment.

The processor may be configured to select the operational software from a software database that includes software corresponding to a plurality of different attachment types.

The device may include a memory, the software database being stored on the memory.

The device may include an interface for receiving updated software.

The drive unit may be configured to stream operational data to the remote console during an actuation of the at least one connection member.

The drive unit may be configured to receive a video data stream from the attachment and transmit the video data stream to the remote console.

The drive unit may be configured to prevent actuation of the actuator if the two-way communication link has not been established.

The power unit may be configured to operate as an FCC-registered device in one or more of the industrial, scientific, and medical (ISM) radio bands.

The industrial, scientific, and medical radio bands include the 2.400 to 2.500 GHz ISM band.

The device may include a plurality of surgical attachments coupleable to the drive unit.

According to an example embodiment of the present invention, a console includes a memory, a processor configured to process data stored on the memory, and a transceiver configured to communicate with a remote surgical instrument. The console is configured to receive identifying data from the surgical instrument, register the surgical instrument based on the identifying data, and establish a wireless two-way communication link between the surgical instrument and the console. The console is also configured to receive at least one of operational data and commands from the surgical instrument and provide operational feedback data to a user of the surgical instrument during the operation of the surgical instrument based on the at least one of operational data and commands.

The console may include a display screen configured to display operational data received from the surgical instrument via the two-way communication link.

The console may have a visual display screen configured to at least one of a) communicate the operational data and b) receive the user commands.

The console may be configured to receive a stream of video data from the surgical instrument.

The console may be configured to output a video signal corresponding to the video data to an external display.

The console may be configured to transfer at least one of a) an operating program and b) firmware to the surgical instrument.

The console may include a programming port configured to output the at least one of a) the operating program and b) the firmware to the surgical instrument.

The console may be configured to record to the memory the operational data received from the surgical instrument.

The console may be configured to communicate the stored data to remote device using a wired connection.

The console may be configured to communicate the stored data via the internet.

According to an example embodiment of the present invention, a method includes wirelessly transmitting identification data from a surgical instrument to a console, registering the surgical instrument with the console, and establishing a two-way wireless communication link between the surgical instrument and the console. The method also includes transferring at least one of operational data and commands between the surgical instrument and the console and providing operational feedback data from the console to a user of the surgical instrument during an operation of the surgical instrument based on the at least one of operational data and commands.

The method may include determining if a signal strength of the wirelessly transmitted identification data is below a predetermined threshold and, if the signal strength is determined to be below the predetermined threshold, requiring a user confirmation prior to the registering.

The method may include maintaining a list on the console of surgical devices that have been registered by the console.

Further details and aspects of example embodiments of the present invention are described in more detail below with reference to the appended figures.

DETAILED DESCRIPTION

Figure 4:
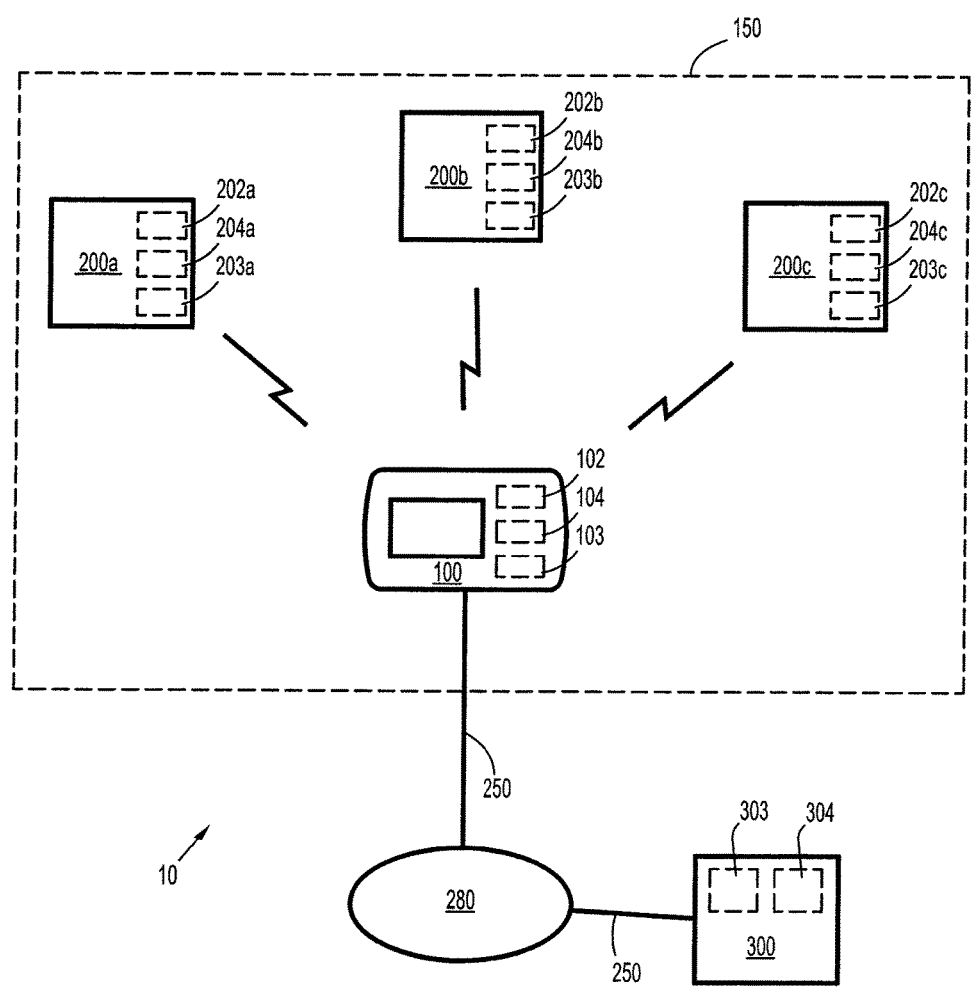
FIG. 4 is a schematic illustration of a system according to an example embodiment of the present invention.

Referring to FIG. 4, a system 10 according to an example embodiment of the present invention is schematically illustrated. The system 10 includes an electronic console 100 that communicates with medical and/or surgical instruments 200a, 200b, and 200c, which are disposed in the same area 150, e.g., the same medical care or surgery room as the console 100. It should be appreciated that the console 100 may communicate with more instruments, e.g., eight or more instruments, and/or less instruments, e.g., a single instrument. However, three instruments, 200a, 200b, and 200c are shown for illustration purposes. These instruments may be, e.g., hand-held surgical instruments (e.g., battery-powered surgical intelligent drive units with interchangeable surgical attachments) or any other medical and/or surgical instrument within communication range of the console 100. The console 100 may be configured to communicate with one surgical instrument 200a, 200b, or 200c at a given time and/or communicate with two or more of the surgical instruments 200a, 200b, and/or 200c simultaneously.

The console 100 provides feedback to an operator of one or more of the instruments, 200a, 200b, and 200c, which may be, e.g., a wireless intelligent power or drive unit 500, described in greater detail below. It also has the capability of recognizing speech and sending wireless commands to the surgical instrument or instruments 200a, 200b, and/or 200c. Upon reception of a wireless command from the surgical instrument, verbal and visual prompts may be displayed, e.g., in multiple languages. The console 100 may receive streaming video from the surgical instrument where the surgical instrument has a video camera, and output the video to a separate video interface pod for display, e.g., on operating room monitors. The console 100 has a circuit board or boards which includes a processor 104 (e.g., an ARM9 class microprocessor), a microcontroller, a serial identification integrated circuit (IC), an audio IC and/or amplifier, a graphics display 110 (e.g., an LCD display), Ethernet interface 140, USB interface 145, a surgical device programming interface (including, e.g., transceiver 102 and/or USB interface 145, illustrated in FIG. 3). It receives its power from an external UL/CE approved AC wall adapter, although it should be understood that other power sources may be provided instead of or in addition to the wall adapter, as described below.

Further, the console 100 may display prompts, e.g., when commanded wirelessly by the surgical instruments, 200a, 200b, 200c on the display 110, e.g., in multiple languages. The console 100 is capable of speaking prompts, e.g., in multiple languages, e.g., when commanded wirelessly by the surgical instruments, 200a, 200b, 200c. The console 100 includes circuitry to update the surgical device software using, e.g., an adapter cable or wireless connection or link. The console may receive these updates over a network, e.g., the Internet and/or an intranet, or any other appropriate mechanism, e.g., via the USB port 145 or a memory card. The console 100 is capable of sending device information, e.g., information related to usage of a surgical attachment such as attachment 600 described detail below. Where, e.g., the attachment 600 a stapler, staple reload and attachment usage data may be transmitted by the console 100 over the Internet.

In an example, the console contains a radio-frequency (RF) receiver capable of receiving surgical instrument transmissions in, e.g., the 400 MHz band and an RF transceiver capable of two-way communications and/or video streaming at 900 MHz to 5.8 GHz bands. The console 100 is capable of processing received streaming video, parameters, and/or prompt information, and outputting streaming video, parameters, and/or prompt information to, e.g., a separate video pod for display (overlay) on external displays, e.g., operating room monitors. The example console 100 contains speech recognition capability that can process voice commands and wirelessly transmit the commands to operate the surgical instruments, e.g., an intelligent power or drive unit 400 described below.

Further, as set forth in greater detail below, the wireless communication may utilize one or more of the industrial, scientific, and medical (ISM) radio bands, e.g., the 2.400 to 2.500 GHz ISM band and the console 100 and/or the surgical instruments 200a, 200b, and 200c may be FCC-licensed to operate in this band. Such ISM band or bands may be used for the unidirectional and/or two-way, or bidirectional, communication between the surgical instruments 200a, 200b, 200c and the console 100. It should be appreciated, however, that the console 100 and/or the surgical instruments, 200a, 200b, 200c may use any appropriate frequency band. Moreover, although this example uses both a unidirectional channel from the surgical instrument 200a, 200b, 200c to the console 100, and a two-way channel between the surgical instruments 200a, 200b, 200c, it should be appreciated that the unidirectional channel may be dispensed with, such that, e.g., all of the communications occur over one or more two-way communication channels or links.

As indicated above, the console 100 communicates wirelessly with each of the instruments 200a, 200b, and 200c via two-way wireless links. In this regard, the console 100 includes a wireless communication device or arrangement 106, including a transceiver 102, to allow two-way wireless communication between the console 100 and the instruments 200a, 200b, and 200c by sending and receiving communication data between the wireless transceiver 102 and each of wireless transceivers 202a, 202b, and 202c of respective wireless communication devices or arrangements 206a, 206b, and 206c corresponding to instruments 200a, 200b, and 200c, respectively. The wireless communication arrangement 106 of this example may also include a receiver in addition to the transceiver. The receiver may be configured to receive unidirectional wireless transmissions from wireless transmitters that may be provided to the instruments 200a, 200b, and 200c. The unidirectional link may utilize a frequency, e.g., a 400 MHz band, that is different from the frequency of the bidirectional or two-way communication link, which may be operated on one or more the ISM bands discussed, or other frequency band.

This unidirectional link may be utilized in different manners. For example, the instruments 200a, 200b, 200c may transmit identification information over the unidirectional link to the receiver of the console 100 and, once electronically registered with console 100, communicate with the console 100 over the two-way communication link. Alternatively, or in addition, the unidirectional communication link may be provided to allow greater bandwidth for communication between the instrument 200a, 200b, 200c and the console 100.

To facilitate various functions, e.g., the storage, processing and/or transmission/receipt of data, the console 100 and each of the instruments 200a, 200b, and 200c include memories 103, 203a, 203b, and 203c, e.g. solid-state and/or disk-based internal memories, to store data, and processors 104, 204a, 204b, and 204c, to, e.g., process the data and initiate transmission/receipt of the data.

As indicated above, the wireless links may utilize one or more of the industrial, scientific, and medical (ISM) radio bands, e.g., the 2.400 to 2.500 GHz ISM band. The console 100 and/or the instruments 200a, 200b, and 200c may be FCC-licensed to operate in this, or any other appropriate ISM band. It should be understood, however, that the console 100 and/or the instruments 200a, 200b, and/or 200c may operate as non-licensed devices that may operate on any appropriate frequency band. Further, the wireless protocol may comply with 802.11b, 802.11g, and/or any other appropriate protocols, standards, or amendments. It is noted that licensed operation over an ISM band, e.g., 2.400 to 2.500 GHz, may be advantageous to limit interference from other devices, e.g., small electronic devices. Moreover, the level of power and the types of data allowed to be communicated may be less restricted over the 2.400 to 2.500 GHz ISM band than some other ISM bands for a registered device.

Figure 1A:
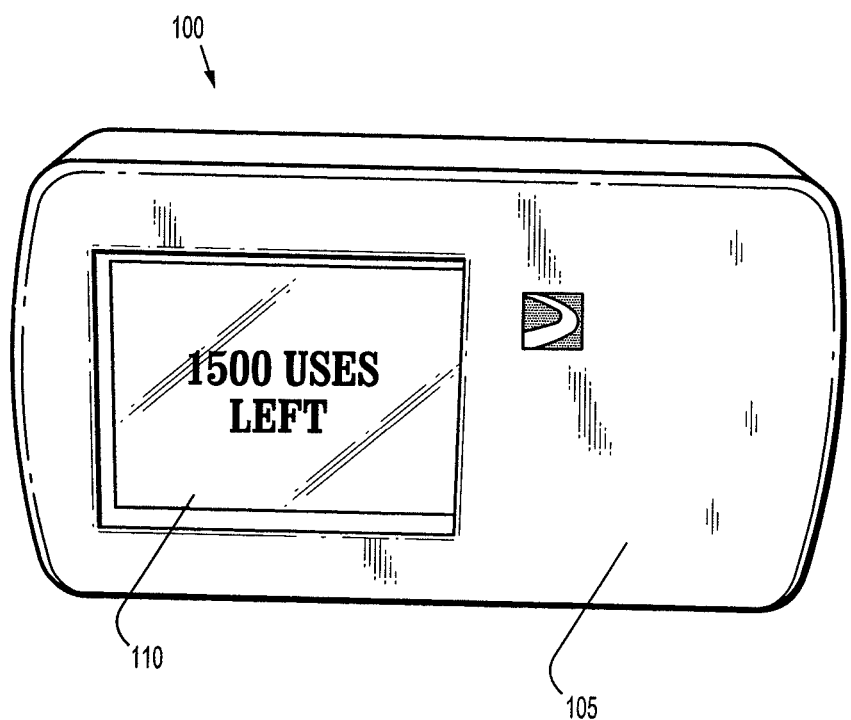
FIGS. 1a to 1c are front views of a console according to an example embodiment of the present invention.
Figure 1B:
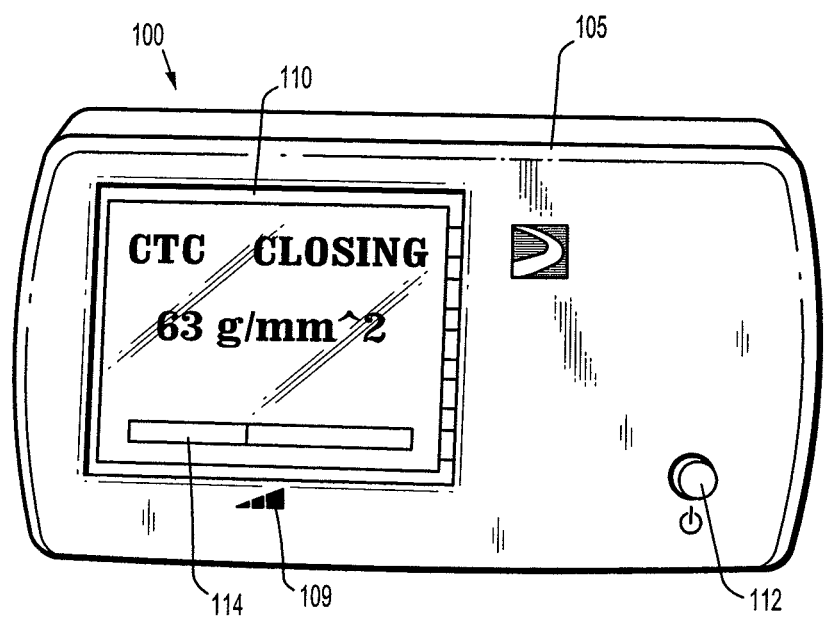
Figure 1C:
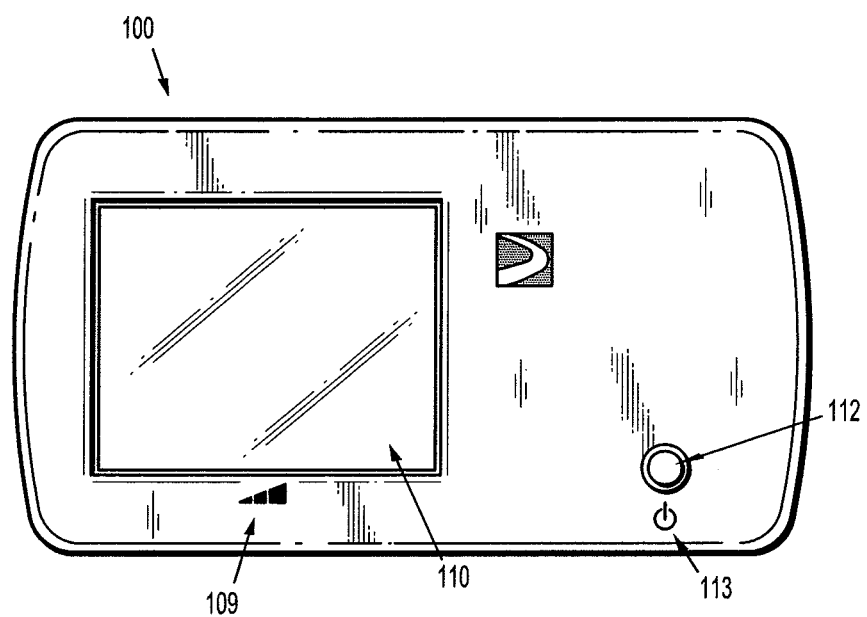

Referring to FIGS. 1a to 1c, a console 100 includes a housing 105. The housing 105 of this example is formed of ABS plastic and has a height of less than 3.25 inches, a width of less than 5.75 inches, a depth of less than 1.75 inches, and a weight of less than 1.5 pounds. It should be understood, however, that the housing may be any appropriate size, dimensions, and weight. The compact size and weight of the housing 105 may be advantageous, however, to enhance the portability and/or stowability of the console 100, flexibility in how and where the console 100 is mounted, and/or to reduce the amount of space consumed, e.g., in an operating room.

A display 110 is disposed on a front face of the housing to provide visual indications to an operator, (e.g., a surgeon) of a surgical instrument or instruments. Although the display 110 is an integrated touch-screen liquid crystal display (LCD), it should be understood that other displays may be provided, e.g., an organic light-emitting diode (OLED) display and/or a non-touch-screen display. The display may be, e.g., a color 320-by-240 line resolution QVGA display, or any other appropriate color or non-color display. Moreover, it should be understood that an integrated visual display need not necessarily be provided. For example, the console may rely solely on auditory communication (e.g., via an audio integrated circuit connected to an integrated speaker 125 or an audio output signal to an external speaker) with the operator and/or may output visual images and/or video to an external display such as, e.g., a monitor in a surgery room.

As indicated below, the example console 100 includes, in addition to the integrated display, an integrated speaker and video output connectors, thus providing flexibility in communicating with the operator. As indicated above, the video output connectors may be used to connect to an external pod and/or display to show, e.g., a streaming video signal received by the console 100 from the surgical instruments 200*a*, 200*b* and 200*c*.

The front of the display also includes a standby switch 112, which may be depressed to place the console 100 into a standby mode or to power down the console. For example, a short press may instruct the console 100 to go into a standby state or to exit the standby state, whereas a long press may instruct the console 100 to power on or off. The standby switch 112 is indicated by a standby symbol 113.

To adjust the volume of auditory indications, e.g., spoken or tonal indications from, e.g., the speaker 125 and/or an audio out line to an external speaker, a volume level display and control 114 is displayed on a lower portion of the display 110. A volume symbol 109 illustrates to the user that the volume increases as the filled portion of the bar of the display and control 114 is moved rightward, and vice-versa. The volume level may be adjusted by the user by, e.g., tapping a particular location on the bar of the volume control 114 to move the filled portion to that location, and/or by touching the screen in the vicinity of the control 114 and performing a sliding motion in a direction corresponding to the desired volume change. For example, if the user touches the control 114 with, e.g., an index finger, and slides the index finger along the screen to the right, the filled portion of the bar may expand by an amount corresponding to the distance of the slide. Likewise, a leftward slide or swipe may cause the filled portion to contract, resulting in a lower volume output. According to an example, there is a one-to-one, or substantially one-to-one, correspondence between the distance of the swipe and the distance the edge of the filled portion or other indicator moves. Other settings, including, e.g., settings related to the operation of the surgical instrument 200*a*, 200*b*, 200*c* and/or settings related to the operation of the console may be adjusted in an analogous manner or in any other appropriate manner, e.g., inputting numerical values using a virtual number pad or keyboard.

Figure 2:
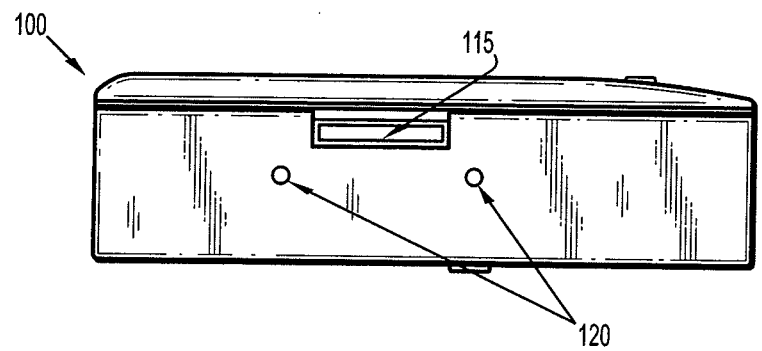
FIG. 2 is a bottom view of the console.

Referring to FIG. 2, the bottom of the console 100 includes a slot 115 for a flash or solid state memory card (e.g., an SD card or any other appropriate memory) and two mounting bracket connectors or holes 120 to receive corresponding connectors of a mounting bracket or brackets to securely hold the console 100, e.g., in a position where the display is viewable by the operator in a surgery room.

Figure 3:
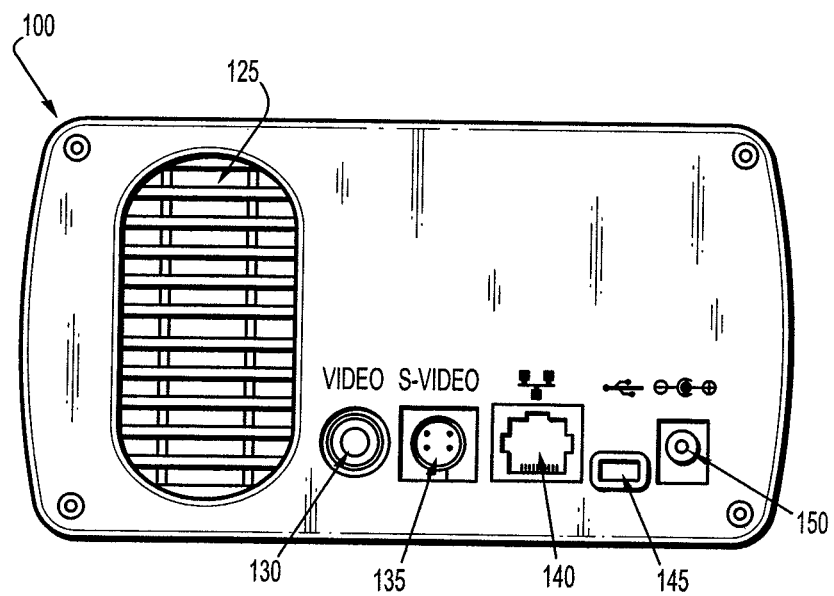
FIG. 3 is a rear view of the console.

Referring to FIG. 3, the rear of the console includes an enclosed speaker 125 for outputting auditory information to the operator. The rear of the console also includes a composite video connector 130 and an S-video connector 135, e.g., a 4-pin mini-DIN, for outputting a video signal to, e.g., an external display and/or recording device. The rear of the console 100 also has a network connector 140. Although the network connector 140 is an Ethernet jack (in this example, RJ-45, IEEE 802.3), it should be appreciated that any appropriate network connector, e.g., a coaxial cable connector, may be used. Although a wireless network connector may be used, a wired connection may allow for more secure communication via the network connector.

The console 100 also has a programming port 145. In this example, the programming port is arranged as a universal serial bus (USB) connector 145. More specifically, the example port 145 is a USB mini-AB port. It should be understood, however, that the programming port may be any type of port that is configured to send and/or receive data, e.g., a coaxial cable, a proprietary connector, and/or a receiver such as, e.g., an infrared receiver and/or other wireless protocol receiver, e.g., a Bluetooth receiver. The programming port 145 is configured to upload software or other data to one or more of the surgical instruments via a data cable and a corresponding connection port on the surgical instrument. It should be appreciated that the USB port may be used as, e.g., a general data port and/or be configured to receive surgical instrument data including software that is used to control the surgical instrument 200*a*, 200*b*, 200*c*. In addition to receiving data, the programming port 145 may be used to transfer data from the console 100 to an external device, e.g., an external hard drive, computer, and/or solid-state memory device.

Software and/or data may be uploaded to the console 100 to be installed on the console 100 and/or the surgical instrument 200*a*, 200*b*, 200*c*. The received data and software may be transferred to the console 100 via the network 280, any appropriate port, e.g., USB port 145, and/or using the wireless communication system, e.g., using transceiver 102.

The received data and software may include, e.g., operating and control algorithms, calibration data, display information, and/or any other software to facilitate operation of the surgical instruments 200*a*, 200*b* and 200*c*. Further, the programming port 145 may be used to install or upgrade console firmware onto the console 100 and/or transfer surgical instrument firmware to the console 100 to be transferred and installed onto the surgical instrument 200*a*, 200*b*, 200*c*.

Power is provided to the console 100 via a power connector 150, which receives a corresponding connector of an AC adapter which plugs into a wall socket. It should be understood, however, that the console 100 may be provided with an internal AC/DC converter and/or may be provided with a battery, e.g., a rechargeable internal or external battery, to provide power. Further, it should be understood that power may be provided by a port such as a USB port, e.g., the programming port 145.

Although particular features are shown as being disposed on a particular face of the housing 105 or at a particular location of the console 100, it should be understood that the any feature or combination of features may be disposed at any appropriate location(s) or face(s) of the housing 105.

Upon powering up, the console 100 performs a self-test and configuration, and then waits to receive communications from one or more instruments, e.g., one or more of instruments 200a, 200b, and 200c. The console 100 may prompt a user or operator to power up a surgical instrument to initiate communications.

Each of the instruments 200a, 200b, and 200c has a serial number that may be stored, e.g., in memory 203a, 204b, 204c. Upon powering up the instrument, e.g., upon inserting a battery pack and/or activating a power switch or button, the instrument begins transmission of data corresponding to its respective serial number. The instruments transmit this information using, e.g., wireless transceivers 202a, 202b, 202c, or the unidirectional communication transmitters as discussed above.

Upon the console 100 receiving the identifying data transmission corresponding to the serial number of the respective instrument 200a, 200b, or 200c, the console 100 displays, via display 110 and/or an external display, the type of instrument and an instrument identifier, e.g., the last three digits of the serial number or the entire serial number. In addition or as an alternative to the visual display of the information, an auditory indication, e.g., a digitized or prerecorded voice from the speaker 125, may convey the information to the user or operator. The console 100 receives the identifying data via, e.g., wireless transceiver 102 or the unidirectional receiver. The console may then prompt the user as to whether or not to register the identified device, or the console may automatically register the device. If the console 100 prompts the user, the user may answer the prompt by, e.g., touching the touch-screen display 110 (e.g., touching a box or graphic labeled "Yes" or "No").

It should be understood that any communication disclosed herein from the console 100 to the user or operator may occur via visual and/or auditory, e.g., verbal, indications using, e.g., any, some, or all of the display device 100, an external display, integrated speaker 125, an external speaker, and/or any other appropriate mechanism.

Where, e.g., the signal received by the console 100 from the instrument is marginal or below a predetermined threshold, the console may prompt the user, requesting an indication or input as to whether or not to register the particular instrument. The user may answer this prompt by, e.g., touching the touch-screen display 110 (e.g., touching a box or graphic labeled "Yes" or "No"). If no response is received, the console 100 may default to a "No" response such that, e.g., further communications from that particular instrument are not recognized and/or acknowledged.

In addition to registration input, the touch-screen may be used to input other console parameters including, e.g., volume and language.

It should be understood that for any user input or command described herein to the console 100 may be performed using appropriate user input mechanism instead of or in addition to the touch-screen display 110, such as, e.g., pressing a separate button and/or speaking (e.g., where the console 100 has a microphone and speech and/or voice recognition software).

The console 100 keeps a record, e.g., in memory 103, of which instruments have been registered with the console 100, and which devices have been refused registration with the console 100. This record may include, e.g., a list of serial numbers corresponding to registered instruments and another list of serial numbers corresponding to unregistered instruments.

The list of registered instruments and/or the list of unregistered instruments may be cleared when the console 100 is powered down or may be retained until, e.g., a user command to delete is entered, a certain amount of time has passed, e.g., since receiving a signal from a particular instrument, and/or a given number of slots are occupied. For example, a list of registered and/or a list of unregistered devices may have, e.g., eight entries, with earliest entries being deleted as later entries are logged. It may be advantageous to maintain the list of unregistered users, e.g., to avoid future prompts for those devices, at least when the received signal is marginal. For example, the list of registered devices may be cleared upon powering down or resetting the device, while a list of unregistered device is stored for future reference.

When an instrument, e.g., one of instruments 200a, 200b, and 200c, is registered with the console 100, the console 100 establishes a two-way wireless communication link. The communication range of the console may be any appropriate range, e.g., a fifteen foot radius, or larger. This two-way communication link allows the console 100 to receive and transmit data including, e.g., commands, to and from the registered surgical instrument or instruments 200a, 200b, and/or 200c. Further, this communication link allows the console 100 to provide an interface with the user, e.g., a surgeon, to display information related to the operation of the device and allows the user to input commands.

For example, the parameters and/or state of one or more components of the device, e.g., the closing rate and/or applied clamping force of clamping jaws of a surgical cutter and stapler, data obtained from sensors and imaging devices, e.g., an image or video display obtained from one or more cameras mounted to an endoscope, and/or any other data.

The user may input commands, e.g., via pressing portions of the touch-screen display 110. These commands may be, e.g., related to the operational parameters of the surgical instrument or instruments 200a, 200b, and/or 200c. For example, for a tissue clamping procedure, the user may input a maximum force, power, and/or closing rate to be exerted on the tissue. The console would then communicate with the surgical instrument or instruments in accordance with the command. For example, the console 100 may set and/or instruct the surgical instrument to set operating parameters of the surgical instrument to achieve operation in accordance with the user's input. These parameters may be set by adding, changing, and/or verifying one or more values or parameters used in the operation of the surgical instrument, e.g., one or more values or parameters used in the software or operating algorithm stored on memory 203a, 203b, and/or 203c, and executed by respective processor 204a, 204b, and/or 204c during operation of the respective surgical instrument 200a, 200b, and/or 200c.

The user may also request particular data related to the surgical instruments 200a, 200b and 200 Where the surgical instrument includes multiple cameras, or where multiple surgical instruments are registered, each having a camera, the user may, e.g., select which view or views to display at a given time.

Further, the operating algorithm disposed in the memory 103, 203a, 203b, and/or 203c and executed by the processor of the console 100 and/or surgical instrument 200a, 200b, and/or 200b may cause the display 110 and/or one or more external displays to display data (e.g., images, numerical data, and/or data indicating a state of the surgical instrument or the patient, etc.), command prompts, and/or menu structure, corresponding to the particular procedure being performed and/or the current stage of the procedure or other conditions.

Further, according to an example, the screen has a virtual button to bring up a menu, where the options available under the menu and/or submenus vary depending on the particular procedure, stage of the procedure, procedure conditions (e.g., based on data from sensors at the surgical site), type of surgical instrument, and/or the state or position of one or more components of the surgical instrument.

The surgical instrument 200a, 200b, and/or 200c may be configured to be surgically operable only when the surgical instrument is registered with the console 100. This may be achieved, e.g., by installing software or firmware onto the memory 203a, 203b, and/or 203c that, when executed by the processor 203a, 203b, and/or 203c, prohibits one or more functions from being performed. For example, the processor 204a, 204b, and/or 204c may be configured to output a control signal and/or voltage to a motor and/or a motor controller only when the software and/or firmware determines that the device has been registered by the console 100 and that the two-way communication link has been established. This determination may be made, e.g., based on communication received by wireless receivers 202a, 202b, 202c.

The surgical instrument 200a, 200b, and/or 200c may periodically or continuously monitor the state of the communication link with the console 100, to ensure that it is still in place. In this regard, the surgical instrument may, e.g., periodically transmit a query signal to the console 100. If the query signal is received by the console 100, the console 100 transmits a response signal to indicate that the query signal was received. Upon receipt of the response signal, the surgical instrument would have verification of the presence of the two-way communication link. The frequency of the queries may be varied, e.g., such that the queries are less frequent or not transmitted at all during certain periods, e.g., if the surgical instrument goes into a standby state due to, e.g., a period of inactivity. Further, such queries may not be needed during periods of data communication between the surgical instrument and the console. Moreover, when data such as, e.g., operational data, software data, image data, or other data is received by either of the surgical instrument and the console, a response signal is transmitted to indicate that the data was received. This may further ensure that the communication link is maintained. The response signals may include, e.g., an identifier so that the receipt of the particular communication (e.g., the particular query signal or data transfer) may be identified and confirmed.

If the surgical instrument 200a, 200b, and/or 200b determines that the communication link has been broken (e.g., due to not receiving a response signal after transmitting one or more query or data transmissions), the surgical instrument may disable some or all functions, partially disable some or all functions, and/or permit certain functions to continue until, e.g., a predetermined time or event occurs. In this regard, the software or firmware of the surgical device may be programmed so that loss of the communication link does not prevent the user, e.g., a surgeon, from completing certain procedures, e.g., where interrupting such procedures may potentially cause complications.

Upon determining that the communication link has been lost, the surgical instrument 200a, 200b, 200c may issue a signal, e.g., an auditory or visual signal that the communication link has been lost. Thus, the user will be alerted and may attempt to re-establish the communication link. The surgical instrument may continue transmitting the query signal, e.g., corresponding to the serial number of the surgical instrument, until a response is received from the console.

The two-way communication link may use any appropriate security or encryption protocol, e.g., Wi-Fi Protected Access (e.g., WPA or WPA2) or Wireless Equivalent Privacy (WEP).

Aside from the wireless communication link with the surgical instruments 200a, 200b, and/or 200c, the console 100 may be configured to send and receive data over a second network 280. The console may send and receive the information to and from a remote device 300, e.g., an off-site computer or server, or a computer or server within the same facility, e.g., within the same hospital, as the server 100. The remote device 300 includes a memory 303 configured to store the data that is received and/or transmitted to and from the console 100, and a processor 304 to process the received data. The remote device may include any other appropriate features, e.g., a display device for viewing the sent and/or received data, and input devices to allow, e.g., manual input (e.g., via a keyboard) and electronic data input. The network 280 may include, e.g., the internet and/or an intranet. It should be appreciated that the console 100 may transmit and receive the data through intermediate devices, e.g., computers or servers (which may or may not process the data before passing the data), between the console 100 and the remote device 300. Further, it should be understood that the console 100 may be configured to communicate directly with device 300 without passing the data over the internet and/or intranet.

Although only one remote device is shown in FIG. 4, it should be understood that any appropriate number of remote devices may be provided. For example, one or more devices 300 may be disposed at the same facility as the console 100, and/or one or more devices may be disposed off-site, e.g., at the site of a surgical equipment administrator.

In the illustrated example of FIG. 4, the console 100 connects to the device 300 over secure wired connections 250. Although the wired connections 250 are Ethernet-based, it should be appreciated that any appropriate wired connection may be provided. It should also be appreciated that, although the illustrated example uses only wired connections, according to some examples, at least one wireless connection may be used. Using only wired connections may be advantageous, however, since a more secure connection may be established to better ensure the privacy of the transmitted data. The data may be transmitted using, e.g., a data encryption protocol that provides a sufficiently secure line of communication between the console 100 and the remote device 300.

The console 100 may transmit to the remote device 300 data related to the operation and/or state of the surgical devices 200a, 200b, and/or 200c. For example, the console 100 may record onto memory 103 data received from the surgical instrument or instruments over the communication network and transmit that data, e.g., with or without processing the data, to the remote device 300. The data may include, e.g., a type of surgical attachment coupled to the surgical device, a serial number of the surgical attachment, a date and/or time of a last use of the surgical attachment, when particular functions were operated, how long particular functions were operated, when and/or for how long user inputs such as triggers or buttons were activated, any error signals and/or indications of abnormal operation, sensor data (e.g., image sensors, temperature sensors, pressure sensors, etc.), identification and/or serial number of a particular insert and/or cartridge (e.g., a staple cartridge of a surgical stapler), a date and/or time of a last use of the particular insert and/or cartridge, a battery level and/or a battery health of the surgical instrument, and/or any other data pertaining to the surgical instrument and/or surgical procedure.

The data may be transmitted to the remote device 300 of a surgical device administrator, which may be, e.g., at a location offsite from the procedure site. The remote device 300 may acquire the data from the console 100 by a periodic transmission at regular intervals and/or transmissions triggered by specific events, e.g., the completion of one or more procedures, before a powering down of the console 100, and/or upon a request or query signal being received by the console 100 from the remote device 100.

The console 100, the remote device 300, and/or the administrator may use the received data for a variety of purposes. According to an example, a cleaning or sanitization status of the surgical device or a component (e.g., a surgical attachment) of the surgical device may be determined. In this regard, a record or database may be maintained regarding cleaning and/or sanitization status for a set of surgical instruments and/or attachments.

This data may be received from a remote device 300, e.g., a computer at a cleaning station, used to record when particular surgical devices are cleaned or sanitized. Upon receiving data from the surgical instrument 200a, 200b, 200c, indicating the particular surgical instrument and/or attachment, e.g., the data corresponding to the surgical instrument's serial number and/or the attachment's serial number, the console may cross reference this identifying data with the cleaning status data to determine if that particular surgical device and/or attachment has been cleaned and/or sterilized since a last previous use. Alternatively, or in addition, the console may send the data to a remote device 300, e.g., a server, which would then process the data to make the determination of whether the particular device or component has been sterilized since a previous use, and then sends the results back to the console 100, which may then proceed to allow the operation of the surgical instrument 200a, 200b, 200c, or disallow the operation.

If the operation is disallowed, the console 100 and/or the surgical instrument may issue an auditory, visual, and/or other alert or notification to indicate that the surgical instrument cannot be operated in its current state. In this manner, the console 100 may prevent the surgical instrument from operating until the cleaning and/or sterilization information is updated to indicate that all appropriate portions of the surgical instrument have been cleaned and/or sterilized.

Further, by tracking the usage and/or malfunction history of the surgical instrument or component, e.g., an attachment, of the surgical instrument, maintenance and servicing of the device may be facilitated. For example, after a certain amount of uses and/or a certain amount of time passes, it may be determined that the surgical instrument 200a, 200b, 200c or an attachment or component of the surgical instrument needs servicing or replacing. If a particular error or malfunction is recorded or after a certain number and/or frequency of errors or malfunctions are recording during use of the instrument or component, it may be determined, e.g., by a software program, that a repair is required. The console 100 may prevent operation of the surgical instrument and/or the user may be alerted by the console or the surgical instrument if the surgical instrument or component of the surgical instrument is due or past due for servicing or is in need of repair.

The console 100 may also track inventory by, e.g., recording a number of staples, cartridges, or other devices used by surgical instrument 200a, 200b, 200c. In an example, the console may correlate a serial number of a staple cartridge to a particular patient. This may allow the staples to be tracked and trends or problems with particular staple batches or types may be identified, e.g., where a substantially high number of patients have complications from procedures using staples from a particular batch and/or type of staples as compared to other batches and/or types of staples. Although staples are mentioned in this example, this tracking procedure may be used to identify trends with other devices.

By tracking the sequence, timing, and duration of commands, and/or other data signals (e.g., images, sensor signals, etc.) according to some examples, the console 100 records an accurate record of a given procedure. This record may be used, e.g., for training purposes and/or to rebut allegations of medical malpractice where, e.g., the record is linked to a particular patient.

It should be understood that a plurality of consoles may be used at a given facility, e.g., at a given hospital. In this situation, data recorded by each of the consoles 100 may be integrated, or combined, with data recorded by each of the other consoles 100, so that, e.g., surgical instruments 200a, 200b, and/or 200c may be accurately tracked despite being registered with different consoles at given times. For example, if the surgical instrument is a hand-held surgical cutter/stapler, the instrument may be used in, e.g., either of two operating rooms, each having its own console 100. This integration, or combining, of data may also facilitate other tracking, e.g. the tracking of the location of surgical instruments, tracking inventory of stock (e.g., staples) for, e.g., automated reordering, etc.

The integration of the data from the different consoles 100 may be performed by a remote device 300, e.g., a computer or server of the surgical device administrator or the hospital and/or by one or more of the consoles 100 (e.g., where the consoles 100 communicate over network 280).

In addition to retrieving the recorded data via the connections 250, the data may be retrieved by accessing a removable memory, e.g., a flash or solid state memory card, from slot 115, onto which the console 100 is configured to write the data, either automatically or upon, e.g., a user command. The removable memory may then be read by a computer, e.g., a remote device 300 and/or a laptop computer by inserting the memory into a memory card reader. It should be further understood that the information may be retrieved via a USB or other data port, e.g., the programming port 145.

Figure 5A:
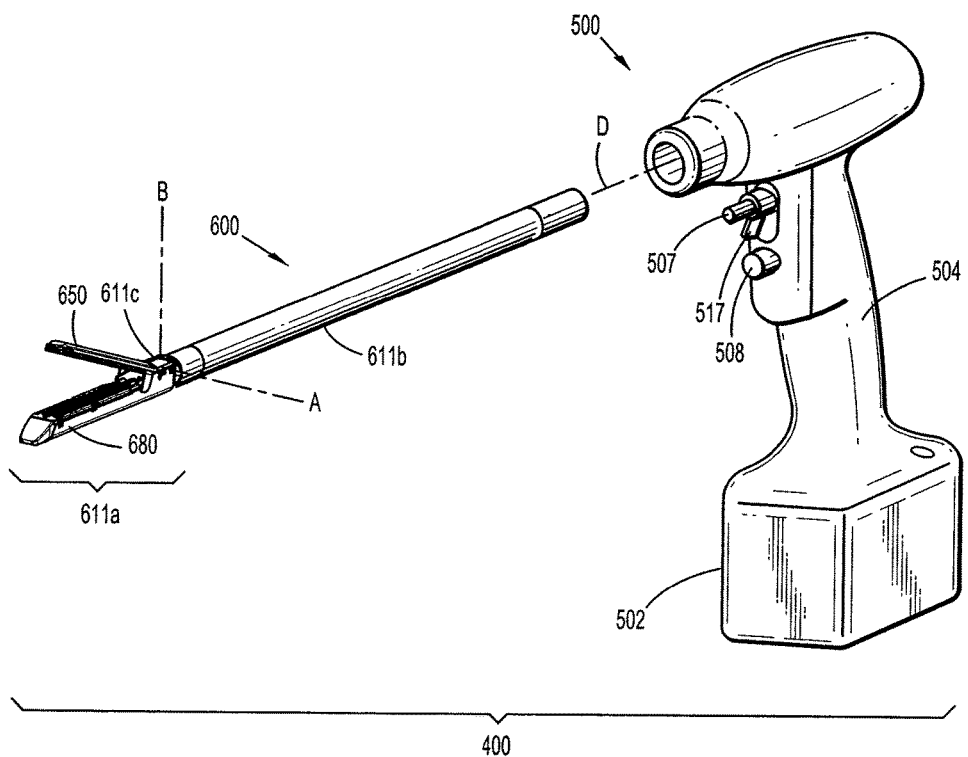
FIGS. 5a and 5b show an intelligent drive unit and a surgical attachment according to an example embodiment of the present invention.
Figure 5B:
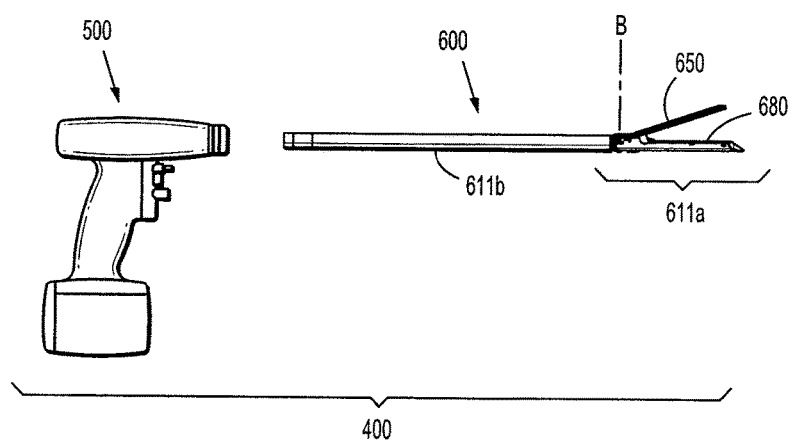
Figure 6:
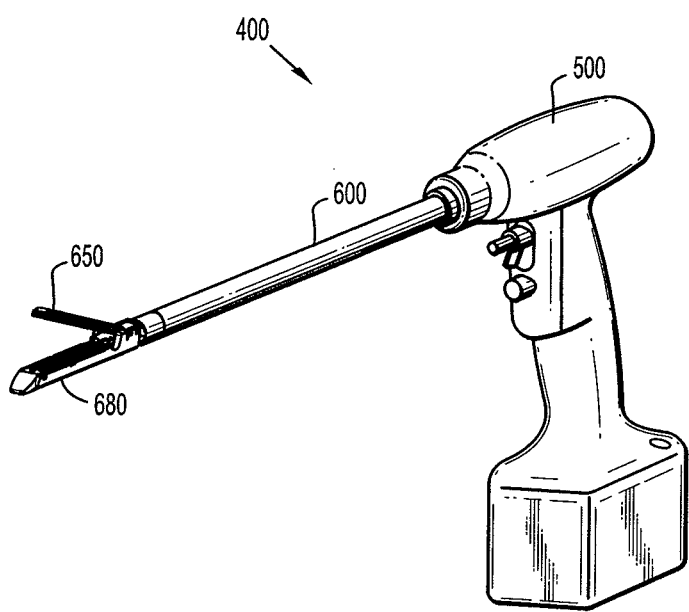
FIG. 6 shows the intelligent drive unit and the surgical attachment when the surgical attachment is connected to the intelligent drive unit.

FIGS. 5a, 5b, and 6 show a surgical instrument 400 including all of the features of surgical instruments 200a, 200b, and 200c described above. The surgical instrument 400 is formed by an intelligent power or drive unit 500 and a removable attachment 600. In this example, the removable attachment 600 is a surgical attachment for clamping, cutting, and stapling tissue. Thus, the attachment 600 mounts to the drive unit 500, as illustrated in FIG. 6, such that the surgical instrument 400 is configured as a hand-held, battery-powered, rotating and/or articulating device for clamping, cutting, and stapling tissue.

Although attachment 600 is removable from intelligent drive unit 500, it should be appreciated that the attachment 600 may be formed to be non-removable from the intelligent drive unit 500.

The surgical instrument 400 is configured so as to be particularly well-suited for insertion into the body of a patient, e.g., via a cannula. As indicated above, in the embodiment shown, the surgical device 400 is a clamping, cutting, and stapling device. The removable attachment 600 of the surgical instrument 400 includes a jaw portion 611*a* that is pivotably coupled to a shaft portion 611*b* by a hinge portion 611*c*. The jaw portion 611*a* includes a first jaw 650 having a distal end and a proximal end, and a second jaw 680 having a distal end and a proximal end. The first jaw 650 and the second jaw 680 are pivotably coupled relative to each other at or near their respective proximal ends. As shown, the first jaw 650 and the second jaw 680 are pivotable relative to each other about pivot axis A. In this arrangement, the jaws are configured such that, upon opening and closing of the first jaw 650 relative to the second jaw 680 and at points in the movement of the first jaw 650 relative to the second jaw 680, both the first jaw 650 and the second jaw 680, e.g., their longitudinal axes, remain within a plane. It should be understood, however, that the attachment 600 may instead be configured such that the first jaw 650 and the second jaw 680 are pivotable relative to each other about a pivot axis that is oriented differently from that shown.

As mentioned above, the jaw portion 611*a* is pivotably coupled to the shaft portion 611*b* by the hinge portion 611*c*. Specifically, the jaw portion 611*a* is pivotable relative to the shaft portion 611*b* about a pivot axis B, which may be positioned at any location on or between the jaw portion 611*a* and the shaft portion 611*b*, and at any circumferential location relative to the jaw portion 611*a* and the shaft portion 611*b*. As illustrated in FIG. 5*b*, the pivot axis B is oriented vertically, and within a plane perpendicular to the viewing angle of the side view shown in FIG. 5. In this arrangement, the jaw portion 611*a* and the shaft portion 611*b* are configured such that, upon articulation of the jaw portion 611*a* relative to the shaft portion 611*b* and at any point in the movement of the jaw portion 611*a* relative to the shaft portion 611*b*, the jaw portion 611*a* and the shaft portion 611*b* remain within a plane that is perpendicular to the pivot axis B. It should be recognized that, in other example embodiments, the pivot axis B may have a different orientation, so as to enable the jaw portion 611*a* to pivot within a different plane. The jaw portion 611*a* may be pivotable to and between any angles relative to the shaft portion 611*b*, such that the jaw portion 611*a* can be selectively positioned as desired during use.

Furthermore, the surgical device 400 may provide rotation of various components about a longitudinal axis of the attachment 600. For example, in various embodiments, the jaw portion 611*a* and/or shaft portions 611*b* may be rotatable relative to the intelligent drive unit 500, which, as illustrated in FIG. 6, is coupled at or near a proximal end of the shaft portion 611*b* of the attachment 600, about a longitudinal axis D of the intelligent drive unit 500, e.g., the longitudinal axis D of the intelligent drive unit 500 at the point where the intelligent drive unit couples to the attachment 600. The shaft portion 611*b* may include a distal portion, to which the jaw portion 611*a* is connected, and a proximal portion, which is toward the intelligent drive unit 500 when the attachment 600 is mounted to the intelligent drive unit 500.

Figure 7A:
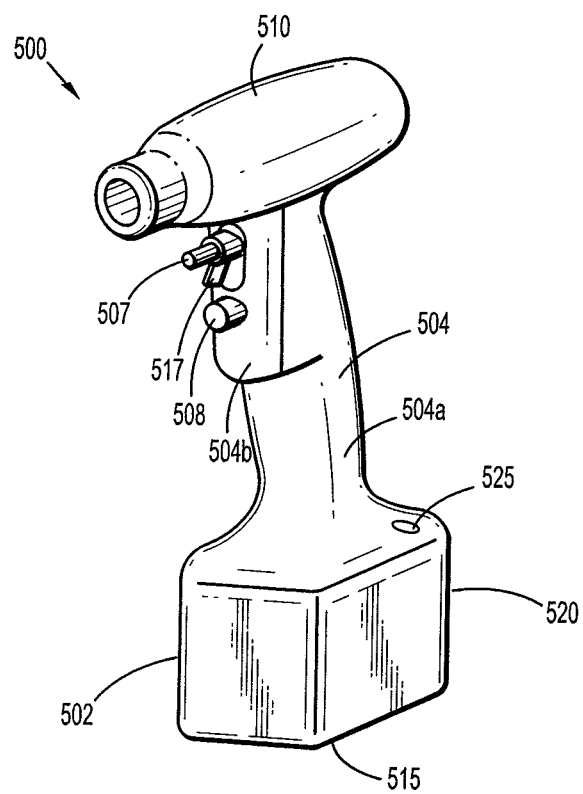
FIGS. 7a and 7b show the intelligent drive unit.
Figure 7B:
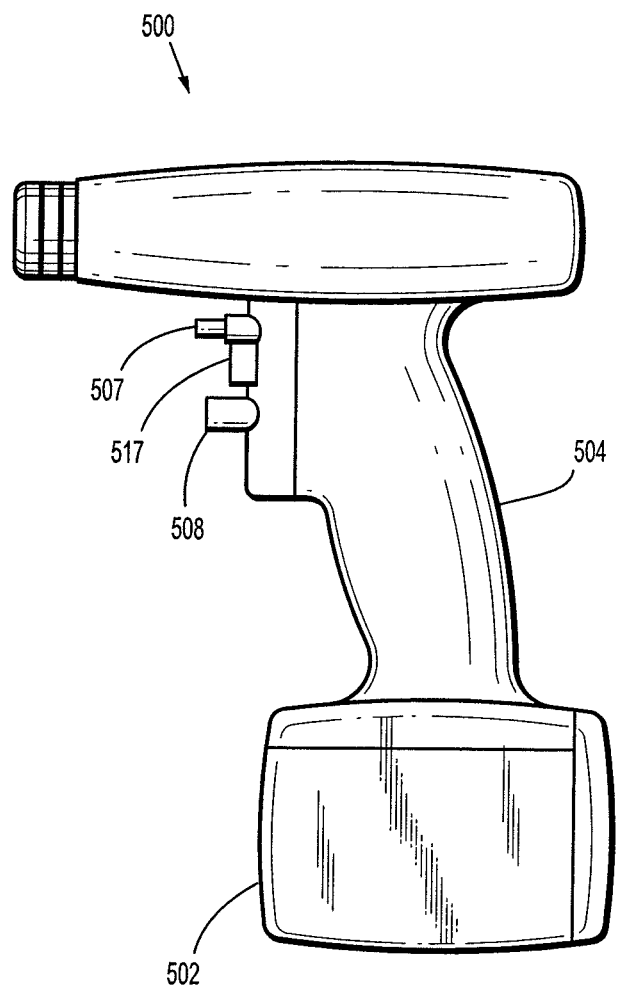

Generally, the handle-shaped profile of the intelligent drive unit 500, as illustrated, e.g., in FIGS. 7*a* and 7*b*, may be grasped by an operator to operate the surgical device 400. The intelligent drive unit 500 has a lower portion 502, which in the embodiment shown, forms a base. In addition, the intelligent drive unit 500 has an intermediate portion 504, which includes several finger-actuated control buttons 507 and 508 and rocker device 517.

Figure 8A:
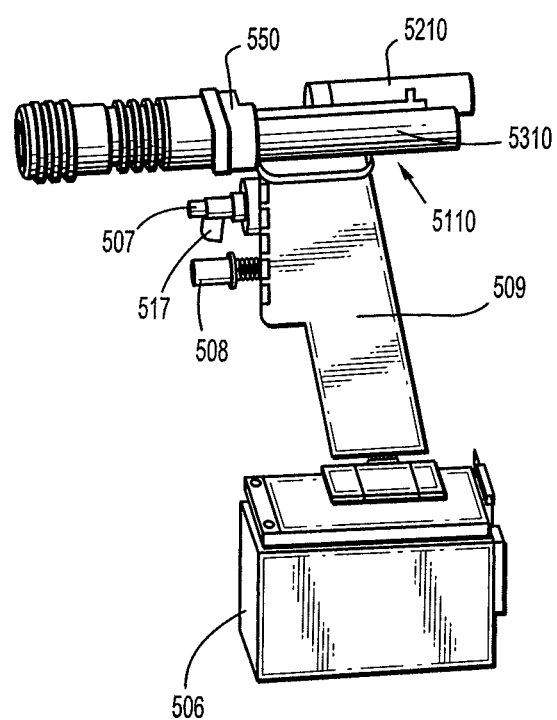
FIGS. 8a to 8c show internal components of the drive unit.
Figure 8B:
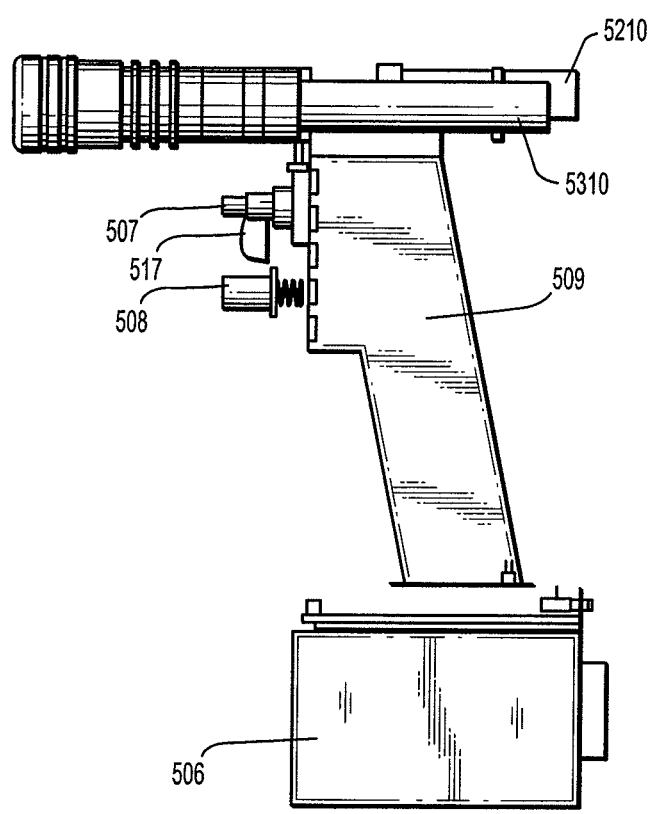
Figure 8C:
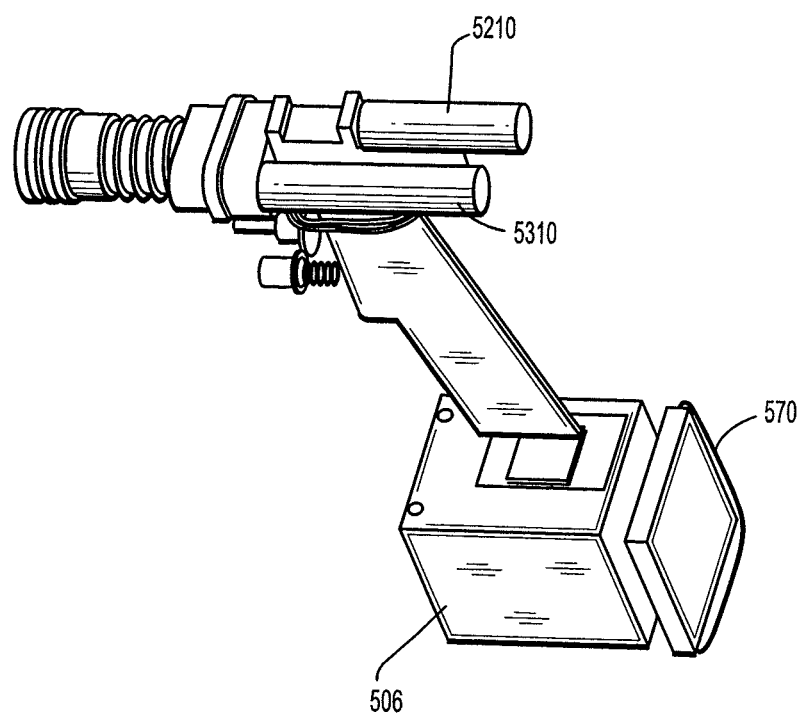

FIGS. 8*a* to 8*c* show internal components of the drive unit 500, showing additional details of the components internal to the intelligent drive unit 500. A power source, e.g., a battery 506, may be situated in the housing provided by the proximal portion 502 of the intelligent drive unit 500. The battery 506 may be configured to supply power to any of the components of the surgical instrument 400. This arrangement may provide an advantage over other surgical devices in that attachment of the surgical instrument 400 to a power source of a separate electro-mechanical surgical system may be eliminated. It should be understood, however, that other example surgical instruments may attach to a separate electro-mechanical surgical instrument to receive mechanical and/or electrical power.

Likewise, the intermediate portion 504 of the intelligent drive unit 500 provides a housing in which a circuit board 509 is situated. The circuit board 509 may be configured to control the various operations of the surgical device 400.

Located at a front location of the intermediate portion 504 of the intelligent drive unit 500 are control buttons 507, 508, and rocker device 517. Each one of the control buttons 507, 508, and rocker device 517 includes a respective magnet that is moved by the actuation of a user, or operator. In addition, the circuit board 509 includes, for each one of the control buttons 507, 508 and rocker device 517, respective Hall-effect switches that are actuated by the movement of the magnets in the control buttons 507, 508 and rocker device 517. For example, located immediately proximal to the control button 507 is a Hall-effect switch that is actuated upon the movement of a magnet within the control button 507 upon the operator actuating the control button 507. The actuation of the Hall-effect switch causes the circuit board 509 to provide appropriate signals to a function selection module 5210 and an actuator or input drive component 5310 to close the first jaw 650 relative to the second jaw 680 and/or to fire a stapling/cutting cartridge within the second jaw 680. For example, depressing button 507 may initiate the closing or clamping of the first jaw 650 relative to the second jaw 680 and depressing button 508 may fire the stapling/cutting cartridge, or vice-versa.

Also, located immediately proximal to the rocker device 517 is a Hall-effect switch that is actuated upon the movement of a magnet within the rocker device 517 upon the operator actuating the rocker device 517. The actuation of the Hall-effect switch causes the circuit board 509 to provide appropriate signals to the function selection module 5210 and the input drive component 5310 to articulate the jaw portion 611*a* relative to the shaft portion 611*b* of the attachment 600. Advantageously, movement of the rocker device 517 in a first direction may cause the jaw portion 611*a* to articulate about axis B relative to the shaft portion 611*b* in a first direction, while movement of the rocker device 517 in a second, e.g., opposite, direction may cause the jaw portion 611*a* to articulate relative to the shaft portion 611*b* in a second, e.g., opposite, direction.

It should be appreciated that any appropriate number of buttons and/or rockers may be provided, e.g., depending on the number and/or type of functions to be performed by various attachments attachable to the intelligent drive unit 500.

Still further, an upper portion of the intelligent drive unit 500 provides a housing in which a drive mechanism 5110 (which includes, e.g., the function selection module 5210 and the input drive component 5310) may be situated. The drive mechanism 5110 may be configured to drive shafts and/or gear components in order to perform the various operations of the surgical device 400, as set forth above. For example, the drive mechanism 5110 may be configured to drive shafts and/or gear components in order to selectively move the jaw portion 611*a* relative to the shaft portion 611*b*, to rotate the shaft portion 611*b* (or portions of the surgical attachment 600 that are distal thereto) about longitudinal axis. D relative to the intelligent drive unit 500, to move the first jaw 650 relative to the second jaw 680, and/or to fire a stapling and cutting cartridge within the second jaw 680.

Figure 9:
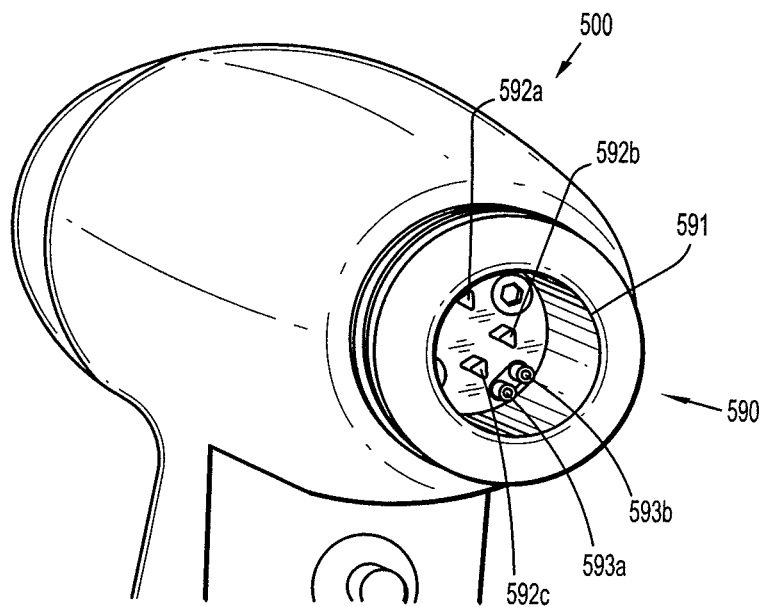
FIG. 9 shows a connecting portion of the drive unit.
Figure 10:
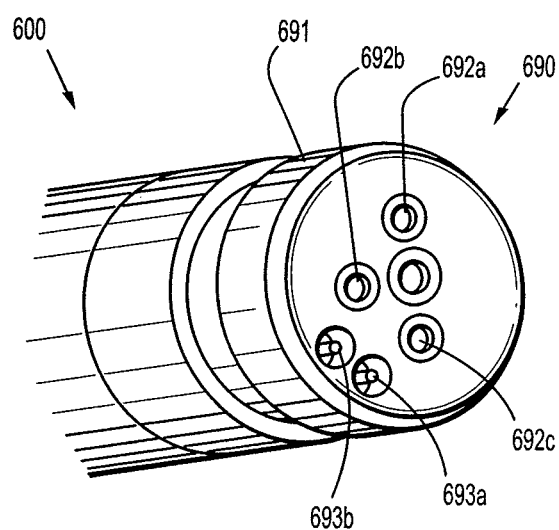
FIG. 10 shows a connecting portion of the surgical attachment.

Referring to FIGS. 9 and 10, the distal portion of the intelligent drive unit 500 includes an attachment interface or connecting portion 590 configured to accept a corresponding interface or connecting portion 690 of the removable attachment 600. The connecting portion 590 of the intelligent drive unit 500 has a cylindrical recess 591 that receives a cylindrical projection 691 of the attachment 600 when the attachment is mated to the intelligent drive unit 500. It should be understood, however, that the connecting portion 690 of the attachment may be provided with a recess to receive a projection of the connecting portion 590 of the intelligent drive unit 500. Moreover, it should be understood that the interface need not be cylindrical and may be of any appropriate shape or geometry.

When the attachment 600 is mated to the intelligent drive unit 500, each of a plurality of rotatable connectors 592*a*, 592*b*, and 592*c* couples with a corresponding rotatable connector 692*a*, 692*b*, 692*c*. In this regard, the interface between corresponding connectors 592*a* and 692*a*, the interface between corresponding connectors 592*b* and 692*b*, and the interface between 592*c* and 692*c* are keyed such that rotation of each of connectors 592*a*, 592*b*, and 592*c* causes a corresponding rotation of the corresponding connector, 692*a*, 692*b*, 692*c*. Although the illustrated interface profiles are approximately triangular, it should be understood that any appropriate geometry may be provided to allow transmission of rotation from the first connectors 592*a*, 592*b*, and 592*c* to respective connectors 692*a*, 692*b*, and 692*c*. It should be further understood that although connectors 592*a*, 592*b*, and 592*c* are provided as male connectors to be inserted into female connectors 692*a*, 692*b*, and 692*c*, connectors 692*a*, 692*b*, and/or 692*c* may be configured to as male connectors configured to be received in respective female connectors 592*a*, 592*b*, and/or 592*c*.

The mating of connectors 592*a*, 592*b*, and 592*c* with connectors 692*a*, 692*b*, and 692*c* allows rotational force to be independently transmitted via each of the three respective connector interfaces. The connectors 592*a*, 592*c*, and 592*a* are configured to be independently rotated by the drive mechanism 5110. In this regard, the function selection module 5210 selects which connector or connectors 592*a*, 592*b*, and/or 592*c* is to be driven by the input drive component 5310 (e.g., an electric motor). It should be understood, however, that one or more of the connectors 592*a*, 592*b*, and/or 592*c* may be provided with a dedicated drive component or motor.

Since each of the connectors 592*a*, 592*b*, and 592*c* has a keyed and/or substantially non-rotatable interface with respective connectors 692*a*, 692*b*, and 692*c* when the attachment 600 is coupled to the intelligent drive unit 500, rotational force or forces may be selectively transferred from the drive mechanism 5110 of the intelligent drive unit 500 to the attachment 600.

The rotational forces may be transferred from the connectors 692*a*, 692*b*, and 692*c* at the proximal end portion of the attachment 600 to the jaw portion 611*a* via a plurality of rotatable drive shafts disposed along the shaft portion 611*b*. The rotatable drive shafts may be non-rotatably coupled, or substantially non-rotatably coupled, at a proximal end to a respective connector 692*a*, 692*b*, or 692*c* and at the distal end to a jaw component or an input of a driver configured to actuate the jaw portion 611*a* or a portion or component thereof. In this manner, the rotatable drive shafts may allow a one-to-one, or substantially one-to-one, transmission of rotation between the connectors 692*a*, 692*b*, and/or 692*c* and the jaw portion 611*a*.

The selective rotation of connectors 592*a*, 592*b*, and/or 592*c* allows the intelligent drive unit 500 to selectively actuate different functions of the attachment. In this example, selective and independent rotation of the three connectors corresponds to the selective and independent articulation of jaw portion 611*a* about axis B, opening and closing of jaws 650 and 680 by rotation of upper jaw 650 about axis A, and driving of a stapling/cutting component of jaw portion 611*a*.

The attachment 600 may couple to the intelligent power unit 500 by any appropriate mechanism. For example, the attachment may latch into place using a slidable latch mechanism (e.g., where a radially outward portion of the power unit 500 is pulled radially rearward or forward to disengage the latch) or a chuck. Although an attachment that requires a separate tool may be provided, it may be advantageous to provide a tool-less, or hand-operated, connection mechanism, e.g., the slide latch described above, a keyless chuck, etc.

The drive mechanism 5110 may include a selector gearbox assembly 550. Proximal to the selector gearbox assembly 550 is the function selection module 5210 that functions to selectively move gear elements within the selector gearbox assembly 550 into engagement with the input drive component 5310. Thus, the drive mechanism may selectively drive one or more of connectors 592*a*, 592*b*, and/or 592*c* at a given time. Although each of the connectors 592*a*, 592*b*, and 592*c* is selectively driven based on an engagement state of the selector gearbox assembly 550, it should be understood that one or more of the connectors 592*a*, 592*b*, and/or 592*c* may be provided with a dedicated drive component or motor.

Regarding the further details of the selector gearbox assembly 550 or of the surgical instrument 400 in general, the surgical instrument 400 includes many features that are substantially the same or analogous to those described in U.S. Published Patent Application No. 2009/0101692, which is expressly incorporated herein in its entirety by reference thereto.

The intelligent drive unit 500 also includes a transceiver coupled to the circuit board 509 and configured to send and receive data transmissions to and from the console 100 as described above with regard to the surgical instruments 200*a*, 200*b*, and 200*c*. The circuit board 509 is configured to disallow operation of various functions, e.g., of the jaw portion 611*b* unless it is determined that a two-way communication link has been established with console 100.

The connecting portion 590 of the intelligent drive unit 500 also includes electrical connectors 593*a* and 593*b* that mate with corresponding electrical connectors 693*a* and 693*b* to allow transmission of electrical signals and/or power between intelligent drive unit 500 and the attachment 600. The electrical connectors 593*a* and 593*b* are electrically coupled to the circuitry, including, e.g., the circuit board 509, to allow the circuitry to receive and/or transmit information and/or electrical power via the electrical connectors 593*a* and 593*b*. The electrical signals may be, e.g., surgical attachment data corresponding to, e.g., a surgical attachment type and/or serial number, a cartridge or insert identifier, sensor data, and/or any other appropriate communication.

This data may be stored on an electronic chip of the surgical attachment and/or a cartridge (e.g., a staple cartridge). For example, a staple cartridge may include an electronic chip including a serial and/or batch number. This information may be read from the chip and relayed to the circuitry of the intelligent drive unit 500 via the interface of the connectors, 593*a*, 693*a*, 593*b*, 693*b*. The circuit board 509 may then transmit, via the transceiver, the data to the console 100 over the two-way communication link, where the console 100 may store and track the data.

Further, the attachment type and serial number may be relayed to the intelligent drive unit 500. This information may be stored, e.g., on an electronic chip of the attachment 600. The circuitry of the intelligent drive unit 500, including, e.g., the circuit board 509, may then communicate this data to the console 100, which may select data including, e.g., an operating program, algorithm, or parameter, and send that data to the circuitry of the intelligent drive unit 500 via the two-way communication link. It should be understood, however, that the circuitry of the drive unit, including, e.g., a memory, may include a plurality of preinstalled programs, algorithms, and/or other parameters from which a selection may be made by the processor 509 to operate the attachment 600.

As indicated above with regard to surgical instruments 200*a*, 200*b*, and 200*c*, the intelligent drive unit 500 may transmit a record to the console 100 of the commands entered by the user, e.g., a surgeon, operating the surgical instrument 400. For example, the intelligent drive unit 500 may transmit to the console 100 signals corresponding to when, how, and/or for how long each of control buttons 507 and 508, and rocker device 517 have been operated during a procedure. The console 100 may then store this information, e.g., on the memory 103. This information may be linked with a particular patient and/or procedure and may be collected, e.g., by an administrator, as indicated above. The intelligent drive unit 500 may transmit this data continuously over the course of the procedure, at predetermined intervals, and/or upon particular events or occurrences, e.g., the end of a procedure or the end of a portion of a procedure.

The intelligent drive unit 500 may also be configured to monitor a parameter of the input drive component 5310. For example, an electric current driving one or more electric motors of the input drive component 5310 may be measured to, e.g., determine a force, e.g., a clamping force, applied by the surgical instrument 400. In this regard, the intelligent drive unit 500 and/or the console 100 may include a control unit or system such as, e.g., that described in U.S. patent application Ser. No. 12/430,780, which is expressly incorporated herein in its entirety by reference thereto. In this regard, the intelligent drive unit 500 may include a current sensor to measure a current driving input drive component 5310, a velocity sensor to determine the rotational velocity of the input drive component 5310, and a position sensor to determine at least one of the position of an output of the input drive component 5310 (e.g., an output shaft of an electric motor), and/or a position of a component (e.g., up per jaw 650 of attachment 600). The control unit may then control the input drive component 5310 based on the inputs from these sensors, e.g., by adjustment of a driving speed of input drive component 5310 by adjusting a voltage applied to the input drive component 5310. Where, e.g., the surgical instrument includes a cutter/stapler attachment 600 as illustrated, the control system may be configured to limit a clamping force exerted by the jaws 650 and 680 onto clamped tissue to a predetermined maximum limit while, e.g., button 507 is depressed by the user.

Based on the sensed and/or determined data and parameters obtained, e.g., during a surgical procedure, the surgical instrument 400 may transmit data to the console 100 over the two-way wireless link, e.g., to be stored, processed, and/or used to provide information to the user of the instrument 400. For example, the closing rate of the jaws 650 and 680 may be transmitted to the console 100 and displayed to the user on the display 110, as illustrated in FIG. 1*b*. The console 100 may also communicate to the user alarms and/or error signals during the procedure based on, e.g., the information transmitted from the surgical instrument 400 to the console 100 over the two-way wireless communication link.

The surgical instrument 400 (more specifically, intelligent drive unit 500) communicates operational data and/or command data to the console 100, to allow the console to provide feedback, including, e.g., instructions, queries, and/or alerts. Operational data may include, e.g., measured or determined values, parameters, statuses, etc., while the command data may be any appropriate instruction to the console 100, e.g., an instruction to query the user, display a status or parameter, and/or issue an alert.

Moreover, the user may set parameters of the surgical instrument 400 by inputting commands into the console 100, which then communicates with the surgical instrument 400 over the two-way wireless communication link based on the user commands. For example, based on an input from a user, the console may transmit data to alter an operating algorithm to use a particular parameter. For example, a user may input a force limit into the console 100 for a clamping procedure. The console 100 may then set the operating parameters of, e.g., the control system described above to cause the surgical instrument 400 to limit the force applied to clamped tissue during the clamping procedure.

The console 100 may be configured to receive user commands and/or prompt the user for commands for any suitable purpose. For example, the user may select from a group of operating programs, modes, and/or algorithms. Based on such commands or input, the console 100 communicates with the surgical instrument 400 over the wireless communication link to, e.g., install operating software and/or set operating parameters. According to an example, for a selected procedure, a program may be communicated to and installed onto the surgical device 400 from the console 100, where the program requires that certain functions be performed in a certain sequence and/or under particular conditions. For example, the circuitry of the surgical instrument 400 may ignore in input signal from a button or other input used to actuate a staple driver (effectively disabling the function of the button) when it is determined that, e.g., a tissue gap between the jaws is not within an acceptable predetermined range.

The console 100 may also alert the user when the battery level and/or health is below a certain threshold. Further, the console 100 and/or the surgical instrument 400 may be configured to prevent certain procedures from beginning when the console 100 and/or the surgical instrument 400 determine that the battery power may not be sufficient to complete that procedure. For example, when a user selects an operating program or mode via, e.g., the touch-screen display 110 and the determination is made (e.g., by the console 100) that the battery level and/or health is not sufficient (based on, e.g., the battery and/or health information transmitted from the surgical instrument 400 to the console 100 over the wireless communication link), the console may indicate to the user that the operation is not permitted based on the current state of the battery, and/or may instruct the user to replace the battery before the procedure may proceed.

Further, as illustrated at FIG. 7a, the intermediate portion 504 of intelligent drive unit 500 is formed of a handle section 504a and a trigger section 504b. The handle section 504a is monolithically formed (e.g., by injection molding) as a single piece, including the tubular portion that receives the user's lower fingers. The trigger section 504b is then joined to the handle section 504a in any appropriate manner (e.g., with adhesive, welding, and/or fasteners). Similarly, an upper housing 510 and a battery housing 515 are each monolithically formed as a single piece and joined to the handle section 504a. The battery 506 is constrained in the battery housing 515 by a battery door 520 that latches into a closed position and is unlatched by depressing a release button 525. As opposed to a construction that joins two approximately symmetric halves along a seam (e.g., a seam that is approximately parallel to the plane of the paper in the view of FIG. 7b), this construction may provide increased strength and may facilitate sealing of the component housing parts 504a, 504b, 510, 515, and/or 520.

The intelligent drive unit 500 is configured to be autoclavable as a unit without any need for disassembly. In this regard, the intelligent drive unit 500, including the battery 506 may be autoclaved without damaging any portion of the intelligent drive unit 500. To facilitate this autoclavability, the intelligent drive unit 500 may include seals or gaskets such as gasket 570 (illustrated, e.g., in FIG. 8c, which is configured to form a hermetic seal between the battery door 520 and the battery housing 515 that is sufficient to prevent moisture from entering the intelligent drive unit housing under the pressure and temperature of an autoclave. Further, the intelligent drive unit 500 and the attachment 600 may be autoclaved together, if desired, when the attachment 600 is coupled to the drive unit 500.

Figure 11:
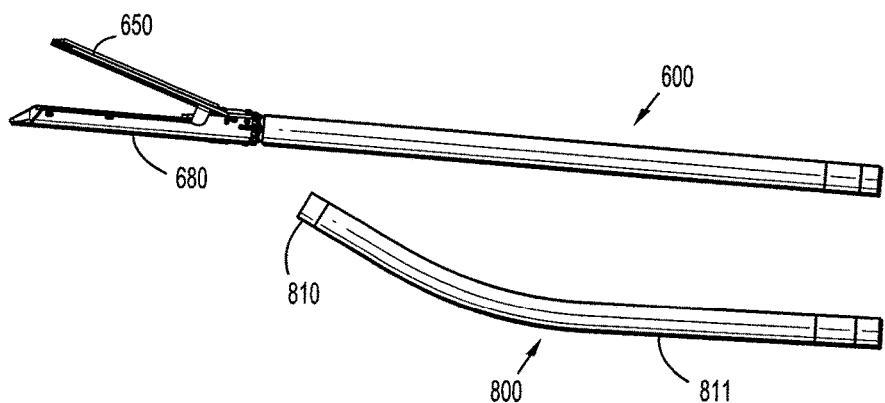
FIG. 11 shows the surgical attachment and an attachment shaft according to an example embodiment of the present invention.

FIG. 11 shows the surgical attachment 600 and a surgical attachment shaft 800 according to an example embodiment of the present invention. Attachment 800 is shown without a jaw or other instrument portion, which may be coupled to a distal end 810 thereof. Attachment shaft 800 differs from the shaft of attachment 600 in that the elongated shaft portion 811 is bent to an angle. This may allow the distal end 810 of the shaft (as well as an instrument attached thereto) to more easily access a portion of a patient's body, e.g., during some endoscopic procedures. Although the attachments 600 and 800 include rigid shafts, it should be understood that flexible shafts may be provided.

Providing a surgical device having power unit 500 to which various attachments may be detachably coupled to be driven provides flexibility in that the same drive unit may be used with different attachments and/or attachment types. In this regard, it is envisioned that an operator, e.g., a surgeon, may use multiple attachments during a single operation. For example, for a bowel cutting, resecting, and stapling operation, a surgeon may first attach a linear cutter/stapler such as attachment 600 to cut and staple at opposite ends of a cancerous portion of tissue to be removed. To rejoin the two sealed ends of the remaining portions of the bowel, the surgeon may swap out the linear stapler/cutter attachment with a circular cutter/stapler attachment by disengaging and removing the linear cutter stapler attachment from the power unit 500 (e.g., by pulling, pushing, and/or turning a latching mechanism or chuck) and then attaching the circular stapler/cutter attachment.

Upon inserting the attachment, the power unit 500 may determine the surgical attachment type and/or the specific surgical attachment, e.g., by reading such data via electrical connectors 693a and 693b from an electronic chip disposed in the attachment. Based on this information, the intelligent power unit 500 and/or the console 100 may select an appropriate operating program and/or set one or more operating parameters.

The power unit 500 and/or the console 100 may cross-reference calibration data associated with a particular attachment. For example, if it has been predetermined that a particular attachment having a particular serial number requires a correction factor to adjust for idiosyncrasies of that attachment, that correction factor may be incorporated into the operating algorithms or programs for that attachment. For example, for a particular attachment type, a full 360-degree rotation of one of the connectors 692a, 692b, 692c may be expected to correlate to an expected displacement or rotation (or other quantifiable state change) of an element, e.g., a jaw 650, at the distal end of the attachment. This expected correlation may be built into the operating programs used for every attachment of that particular type. If, however (e.g., during testing), it is determined that a particular unit requires slightly more or slightly less rotation than the 360-degree rotation to achieve the expected effect, a correction factor may be provided to account for this quality of the individual attachment when the attachment is operated.

Figure 12:
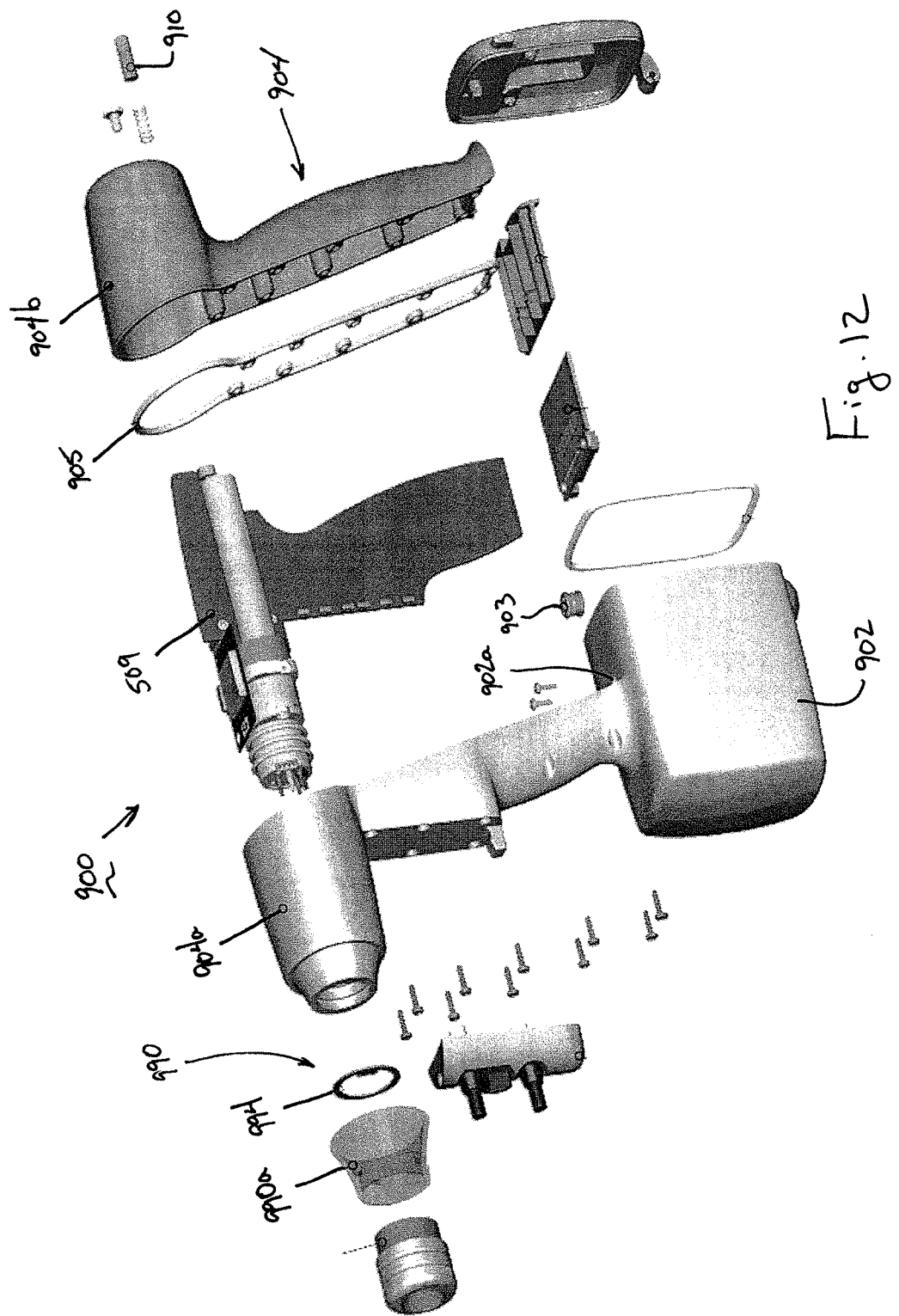
FIG. 12 is a perspective view, with parts separated, of an intelligent drive unit according to another embodiment of the present disclosure.

Turning now to FIG. 12, an alternate embodiment of an intelligent drive unit is generally shown as 900. Intelligent drive unit 900 is substantially similar to intelligent drive unit 500 and thus will only be described in detail herein to the extent necessary to identify differences in construction and/or operation thereof.

As seen in FIG. 12, intelligent drive unit 900 includes an intermediate portion 904 extending from and/or supported on a lower portion 902. Intermediate portion 904 includes a distal half-section 904a integrally formed with and extending from the lower portion 902, and a proximal half-section 904b connectable to distal half-section 904a by a plurality of fasteners. Distal and proximal half-sections 904a, 904b define a housing having a cavity therein in which circuit board 509 is situated.

Distal and proximal half-sections 904a, 904b are divided along a plane that is substantially orthogonal to longitudinal axis "D," as seen in FIG. 5a.

Intermediate portion 904 further includes a gasket 905 extending completely around a rim of proximal half-section 904b and being interposed between distal half-section 904a and proximal half-section 904b. Gasket 905 seals the perimeter of distal half-section 904a and proximal half-section 904b.

In this manner, the cavity of intermediate portion 904 is sealed along the perimeter of distal half-section 904a and proximal half-section 904b yet is configured to enable easier, more efficient assembly of intelligent drive unit 900 and easier, more efficient service, maintenance or repair of intelligent drive unit 900.

Lower portion 902 of intelligent drive unit 900 defines an aperture 902a formed in an upper surface thereof and which is located beneath intermediate portion 904. Aperture 902a provides a passage through which wires (not shown) pass to electrically interconnect electrical components (battery, circuitry, etc.) situated in lower portion 902 with electrical components (motor, circuitry, etc.) situated in intermediate portion 904. Lower portion 902 includes a gasket 903 disposed within aperture 902a thereby plugging or sealing aperture 902a while allowing the wires to pass therethrough.

It is envisioned that the wires may be potted within gasket 903 to help maintain the position of the wires therein.

Intermediate portion 904 defines a nose or connecting portion 990. Nose portion 990 includes a nose cone 990a supported on a distal end of intermediate portion 904. Nose cone 990a is fabricated from a transparent, semi-transparent and/or translucent material. Nose portion 990 includes an illumination member 994 disposed within nose cone 990a such that illumination member 994 may be seen or may be visible therethrough. Illumination member 994 may be in the form of a light emitting diode printed circuit board (LED PCB) or the like. Illumination member 994 may be configured to illuminate at least one, and desirably multiple colors with each color being associated with a unique discrete event.

As seen in FIG. 12, intelligent drive unit 900 includes a fire button or safety switch 910 situated at a proximal end of intermediate portion 904. In use, surgical attachments 600 may be actuated between opened and closed conditions as needed and/or desired. However, in order to fire surgical attachment 600, in order to expel fasteners therefrom, with surgical attachment in a closed condition, safety switch 910 is depressed thereby instructing intelligent drive unit 900 surgical attachment 600 may be fired to expel the fasteners therefrom.

Figure 13:
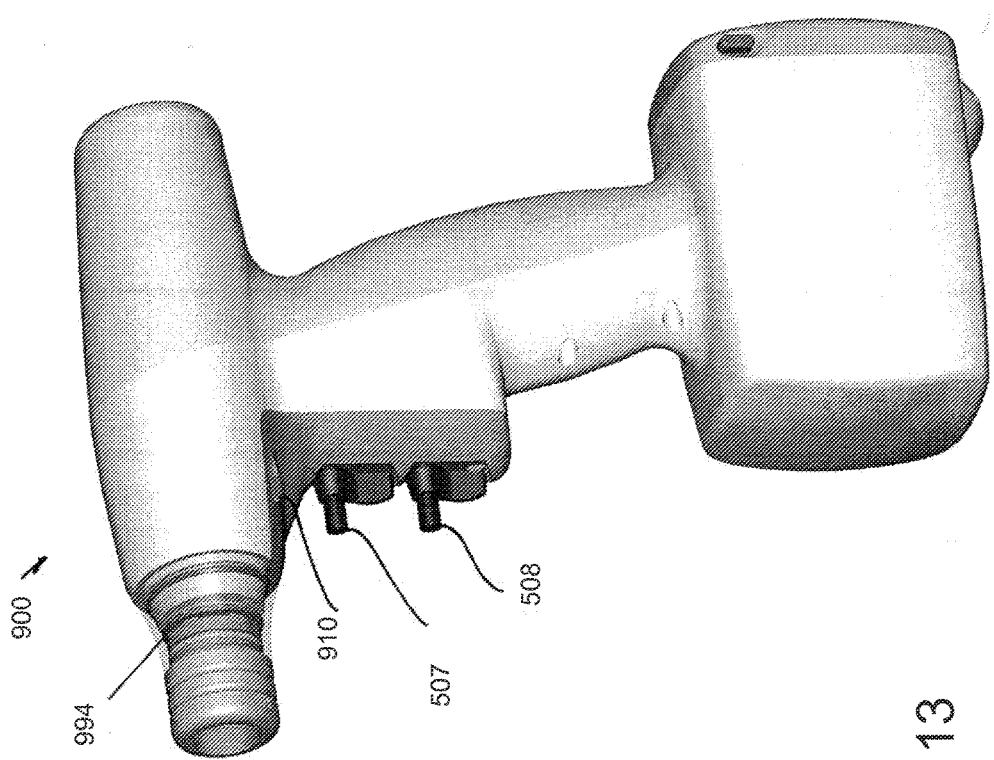
FIG. 13 is a perspective view of an intelligent drive unit according to yet another embodiment.

As seen in FIG. 13, safety switch 910 may be located near a distal end of intermediate portion 904. In particular, safety switch 910 is shown disposed in close proximity to control buttons 507, 508 and may be actuatable from either side of intermediate portion 904.

In order minimize accumulative error, it is contemplated that the initial position of the selector shifter and, when attached, any adapters interposed between the intelligent drive unit 900 and the attachment 600, may also be calibrated.

Although surgical stapler/cutters are described herein as exemplary surgical attachments, it should be understood that any of a large variety of types of surgical attachments may be provided to and powered by the drive unit 500.

For attaching the attachments, it may be advantageous for the attachments to securely latch into the drive unit 500 by pressing the attachments axially into the drive unit. Further, as indicated above, a tool-less attachment and detachment mechanism may be particularly advantageous in simplifying attachment, detachment, and exchange of surgical attachments from the drive unit 500.

Although the present invention has been described with reference to particular examples and exemplary embodiments, it should be understood that the foregoing description is in no manner limiting. Moreover, the features described herein may be used in any combination.

What is claimed is:

1. A surgical device, comprising:
a hand-held, battery-powered drive unit including:
a housing defining a longitudinal axis aligned with a shaft of a surgical attachment upon coupling the surgical attachment to the drive unit, the housing including:
a base portion including an upper wall defining an aperture therethrough;
a distal half-section including:
an upper portion extending upwardly from the upper wall of the base portion; and
a lower portion extending substantially perpendicularly from the upper portion;
a proximal half-section selectively securable to the distal half-section, the distal half-section and the proximal half-section separated along a plane that is transverse to the longitudinal axis of the housing, the proximal half-section including:
an upper portion; and
a lower portion extending substantially perpendicularly from the upper portion of the proximal half-section;
a first gasket interposed between the distal and proximal half-sections; and
a second gasket interposed within the aperture of the base portion;
a mounting portion provided in the distal half-section, the mounting portion configured to accept a corresponding portion of the surgical attachment; and
an integral unit of internal components configured for removable receipt in the housing, the integral unit of internal components including:
a drive mechanism configured for receipt in both the upper portion of the distal half-section and the upper portion of the proximal half-section; and
a circuit board configured for receipt in at least both the lower portion of the distal half-section and the lower portion of the proximal half-section.

2. The surgical device according to claim 1, wherein the housing of the drive unit includes an actuator configured to actuate at least one connection member, the connection member mating with a corresponding portion of a surgical attachment when the surgical attachment is mounted to the mounting portion to allow the actuation of the at least one connection member to drive the surgical attachment.

3. The surgical device according to claim 1, wherein the distal half-section of the housing is integrally formed with the upper wall of the base portion.

4. The surgical device according to claim 1, wherein the drive unit includes a safety switch supported on the housing, wherein the surgical device can only be fired after the safety switch is actuated.

5. The surgical device according to claim 1, further comprising an illumination member disposed on the mounting portion, wherein the illumination member illuminates upon an occurrence of a predetermined event during operation of the surgical device.

6. The surgical device according to claim 5, wherein the illumination member is configured to illuminate a plurality of different colors corresponding to a plurality of different predetermined events during operation of the surgical device.

7. The surgical device according to claim 1, wherein each of the proximal and distal half-sections has a face, the face of the proximal half-section defining an opening therein and including a mating surface, the face of the distal half-section defining an opening therein and including a mating surface configured to mate with the mating surface of the proximal half-section.

8. The surgical device according to claim 7, wherein the proximal and distal half-sections of the housing cooperatively define a cavity therein.

9. The surgical device according to claim 1, wherein an internal cavity defined in the base portion is in fluid communication with an internal cavity defined in the lower portion of the distal half-section via the aperture.

10. The surgical device according to claim 1, wherein the lower portion of the distal half-section extends substantially perpendicularly upward from the upper wall of the base portion.

11. The surgical device according to claim 10, wherein the lower portion of the distal half-section has an outer periphery, and the upper wall of the base portion has an outer periphery surrounding the outer periphery of the lower portion of the distal half-section.

12. The surgical device according to claim 1, wherein upon coupling the proximal and distal half-sections to one another the upper portion of the proximal half-section is aligned with the upper portion of the distal half-section along the longitudinal axis, and the lower portion of the proximal half-section and the lower portion of the distal half-section are parallel.

13. The surgical device according to claim 1, wherein the integral unit of internal components further includes at least one button attached to the circuit board and extending distally out of the lower portion of the distal half-section.

* * * * *